US012728291B2

(12) United States Patent
Murakami et al.

(10) Patent No.: US 12,728,291 B2
(45) Date of Patent: Sep. 8, 2026

(54) ULTRASONIC THERAPY DEVICE, FLUID OPERATION DEVICE, AND FLUID CIRCUIT SET

(71) Applicants: HIRATA CORPORATION, Kumamoto (JP); SONIRE Therapeutics Inc., Tokyo (JP)

(72) Inventors: Seigo Murakami, Kumamoto (JP); Kenji Morita, Kumamoto (JP); Taiga Taketsu, Kumamoto (JP); Jun Okamoto, Tokyo (JP)

(73) Assignees: HIRATA CORPORATION, Kumamoto (JP); SONIRE THERAPEUTICS INC., Tokyo (JP)

( * ) Notice: Subject to any disclaimer, the term of this patent is extended or adjusted under 35 U.S.C. 154(b) by 13 days.

(21) Appl. No.: 18/855,681

(22) PCT Filed: Apr. 12, 2023

(86) PCT No.: PCT/JP2023/014865
§ 371 (c)(1),
(2) Date: Oct. 10, 2024

(87) PCT Pub. No.: WO2023/199947
PCT Pub. Date: Oct. 19, 2023

(65) Prior Publication Data

US 2025/0303196 A1 Oct. 2, 2025

(30) Foreign Application Priority Data

Apr. 14, 2022 (WO) .................. PCT/JP2022/017845

(51) Int. Cl.
*A61N 7/00* (2006.01)
*A61B 34/30* (2016.01)

(52) U.S. Cl.
CPC ................ *A61N 7/00* (2013.01); *A61B 34/30* (2016.02)

(58) Field of Classification Search
CPC .... A61N 7/00; A61N 7/02; A61N 2007/0086; A61B 34/30; A61B 2017/2253; A61B 2090/064
See application file for complete search history.

(56) References Cited

U.S. PATENT DOCUMENTS 5,025,215 A * 6/1991 Pirl ...................... G01N 29/225
73/866.5
5,560,362 A * 10/1996 Sliwa, Jr. ............ G10K 11/004
600/459

(Continued)

FOREIGN PATENT DOCUMENTS

CN 202387036 U 8/2012
JP H02104345 A 4/1990

(Continued)

OTHER PUBLICATIONS

Office Action mailed on Nov. 7, 2023 by the Taiwanese Patent Office in corresponding Patent Application No. 112113852, partial translation. (7 pages).

(Continued)

*Primary Examiner* — Hien N Nguyen
(74) *Attorney, Agent, or Firm* — .Buchanan Ingersoll & Rooney PC

(57) ABSTRACT

An ultrasonic therapy device includes a robot arm, an ultrasonic head unit that includes a wave source which radiates ultrasonic waves in a manner of focusing at a predetermined position inside a therapy object, and a fluid circuit section that includes a plurality of flow path members for circulating a medium liquid. The fluid circuit section includes a circuit control instrument section which causes the medium liquid to circulate through the plurality of flow (Continued)

path members, and an instrument attachment section on which the circuit control instrument section is attached at a predetermined position. The circuit control instrument section is attached to one surface side of the instrument attachment section, and the plurality of flow path members are provided in an attachable/detachable manner with respect to the circuit control instrument section.

18 Claims, 18 Drawing Sheets

(56) References Cited

U.S. PATENT DOCUMENTS

| | | | | |
|---|---|---|---|---|
| 6,261,231 | B1 | 7/2001 | Damphousse et al. | |
| 10,010,722 | B2 | 7/2018 | Wing et al. | |
| 2001/0022585 | A1* | 9/2001 | Endo .................... | G01C 21/367 701/25 |
| 2007/0006656 | A1* | 1/2007 | Batzinger ............ | G01N 29/262 73/606 |
| 2008/0077056 | A1 | 3/2008 | Kagosaki et al. | |
| 2008/0146996 | A1* | 6/2008 | Smisson ............. | A61M 1/0281 604/113 |
| 2010/0094192 | A1 | 4/2010 | Peters et al. | |
| 2011/0072970 | A1 | 3/2011 | Slobodzian et al. | |

FOREIGN PATENT DOCUMENTS

| | | | |
|---|---|---|---|
| JP | H0614955 | A | 1/1994 |
| JP | 3001188 | U | 6/1994 |
| JP | 2013505786 | A | 2/2013 |
| JP | 2014-208309 | A | 11/2014 |
| JP | 2019162414 | A | 9/2019 |
| JP | 2020036709 | A | 3/2020 |
| TW | 201408348 | A | 3/2014 |
| WO | 2020203317 | A1 | 10/2020 |

OTHER PUBLICATIONS

Office Action (Notice of Allowance) and English translation of the Search Report issued on Apr. 14, 2025, in corresponding Taiwanese Patent Application No. 113118076. (4 pages).

International Search Report (PCT/ISA/210) with translation and Written Opinion (PCT/ISA/237) mailed on Jun. 13, 2023, by the Japanese Patent Office as the International Searching Authority for International Application No. PCT/JP2023/014865. (13 pages).

Office Action mailed on Jun. 25, 2024 by the Japanese Patent Office in corresponding Patent Application No. 2024-076181, partial translation. (4 pages).

Office Action mailed on Nov. 4, 2023 by the Taiwanese Patent Office in corresponding Patent Application No. 112113852, partial translation. (7 pages).

European Search Report dated Mar. 13, 2026, issued in corresponding European Patent Application No. 23788365.7 (13 pages).

* cited by examiner 29A
29
29B
29D (29C)
R1A
29E (29C)
R2B
25A1
25A
21
R1
28C
R4
T
25B
R5
27E
25A3
27F
27D
R2
26B
27C
26A
25
28B
R3
R2
27A
R2
27B
28BB
28A
21B
25A2
14
14RA
14RB
R1B
R2A

ULTRASONIC THERAPY DEVICE, FLUID OPERATION DEVICE, AND FLUID CIRCUIT SET

Priority is claimed on International Patent Application PCT/JP2022/017845, filed Apr. 14, 2022, the content of which is incorporated herein by reference.

TECHNICAL FIELD

The present invention relates to an ultrasonic therapy device, a fluid operation device, and a fluid circuit set for performing ultrasonic-based therapy for a therapy object.

BACKGROUND ART

Ultrasonic therapy devices which perform therapy by radiating ultrasonic waves to an affected part of a therapy object such as a patient are known (for example, refer to Patent Documents 1 and 2). The ultrasonic therapy device described in Patent Document 1 includes a robot arm that is formed with links joined by a plurality of joints, an ultrasonic head unit that is supported by a tip of the robot arm and includes an emission portion emitting ultrasonic waves to an affected part, and a control device that controls the robot arm and the ultrasonic head unit.

For example, an ultrasonic wave generation source, which radiates ultrasonic waves to an affected part inside the body of a patient supported by a therapy bed, is provided at a tip of the ultrasonic head unit. For example, the ultrasonic head unit described in Patent Document 2 includes an ultrasonic head unit that includes a head casing including an ultrasonic wave generation source, and a flexible contact member that is provided in the head casing and formed to have a bowl shape so as to cover an opening for exposing a wave source. The contact member is brought into contact with a part at a position on a body surface on an extended line passing through an affected part inside the body of a patient. In the head casing of the ultrasonic head unit, a mounting portion for mounting the contact member is provided, and a liquid storage section is formed by mounting the contact member in the mounting portion such that a tip portion of an ultrasonic head is filled with a medium liquid transmitting ultrasonic waves. In addition, flow path members which are used during supply of a medium liquid or discharge of a medium liquid with respect to the liquid storage section are connected to the head casing.

CITATION LIST

Patent Document

Patent Document 1: Japanese Unexamined Patent Application, First Publication No. 2020-036709

Patent Document 2: Japanese Unexamined Patent Application, First Publication No. 2019-162414

SUMMARY OF INVENTION

Technical Problem

For the sake of hygiene management, it is desirable that a contact member which comes into contact with the body of a patient be replaced and used for each patient. Regarding flow path members which are connected to a liquid storage section for supplying a medium liquid to a liquid storage section covered by the contact member, and a liquid container which is connected to the flow path members and accommodates the medium liquid, since the ultrasonic transmission performance deteriorates if air bubbles are mixed into a medium liquid, it is desirable to replace them for each patient. In addition, a medium liquid comes into contact with air remaining in the flow path members through usage over time so that the amount of dissolved oxygen gradually increases. Since the ultrasonic transmission performance deteriorates if the amount of dissolved oxygen in a medium liquid increases, it is also desirable to replace the medium liquid for each patient. In addition, regarding the contact member and the flow path members, since loads applied to the members vary depending on the situation of therapy and there is also a probability of breakage during therapy if they are used continuously over a plurality of times of therapy, it is desirable to replace them for each therapy.

According to the technologies in the related art, when ultrasonic therapy is performed, it is necessary that replacement work of a contact member, a liquid container, and flow path members and work of liquid discharge and liquid supply with respect to a liquid storage section be manually performed for each patient, and this may lead to increase in workload. In addition, regarding preparation for therapy after replacement, work of passing water through the liquid storage section and performing degassing processing may also take time.

An object of the present invention is to provide an ultrasonic therapy device, a fluid operation device, and a fluid circuit set in which work efficiency of replacement work and work of supplying and discharging a medium liquid when a contact member, flow path members of a fluid circuit section, and a liquid container for circulating a liquid are replaced for each therapy can be improved.

Solution to Problem

An aspect of the present invention is an ultrasonic therapy device including a robot arm that includes a plurality of arm members joined with a plurality of joints, moves a holding target to an arbitrary position, and is capable of holding the holding target in an arbitrary posture state; an ultrasonic head unit that is held by the robot arm and includes a wave source which radiates ultrasonic waves in a manner of focusing at a predetermined position inside a therapy object and a liquid storage section which includes a contact portion whose lower surface side comes into contact with the therapy object and is formed to have an adjustable volume; and a fluid circuit section that includes a plurality of flow path members for circulating a medium liquid which fills the liquid storage section and transmits the ultrasonic waves. The fluid circuit section includes a circuit control instrument section which causes the medium liquid to circulate through the plurality of flow path members, and an instrument attachment section in which the circuit control instrument section is attached at a predetermined position. The circuit control instrument section is attached to one surface side of the instrument attachment section, and the plurality of flow path members are provided in an attachable/detachable manner with respect to the circuit control instrument section. The fluid circuit section includes a first circuit portion which causes the medium liquid to circulate through the plurality of flow path members, and a second circuit portion which causes gas to flow into the first circuit portion from the outside. The first circuit portion includes an inflow circuit portion which causes the medium liquid to flow into the liquid storage section, an outflow circuit portion which causes the medium liquid to flow out from the liquid storage section, and a discharge circuit portion which discharges the medium liquid to the outside.

Advantageous Effects of Invention

According to the present invention, it is possible to improve work efficiency of replacement work and work of supplying and discharging a medium liquid when a contact member, flow path members of a fluid circuit section, and a liquid container for circulating a liquid are replaced for each therapy.

BRIEF DESCRIPTION OF DRAWINGS

FIG. 17 is a perspective view showing a casing according to Modification Example 1 of the present invention.

DESCRIPTION OF EMBODIMENT

Figure 1:
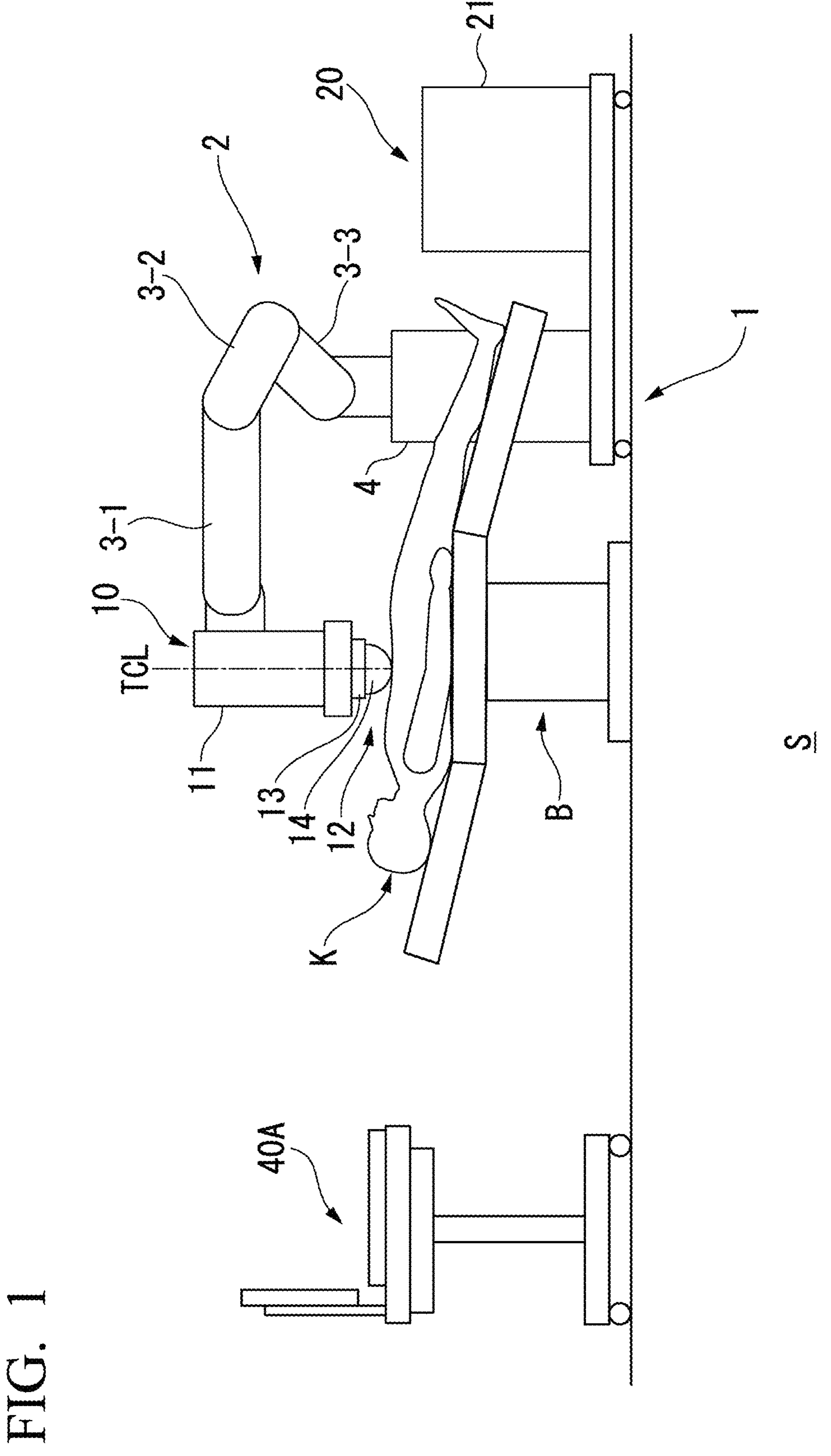
FIG. 1 is a view showing a schematic constitution of an ultrasonic therapy system.

As shown in FIG. 1, an ultrasonic therapy system S includes an ultrasonic therapy device 1 which controls emission of ultrasonic waves, and a management control device 40A which operates the ultrasonic therapy device 1 and manages the usage state thereof. In addition, the ultrasonic therapy system S includes a therapy bed B which supports a patient K who is to be a therapy object. The ultrasonic therapy device 1 includes a robot arm 2 which supports and moves a target, an ultrasonic head unit 10 which is provided at a tip portion of the robot arm 2 as a target, and a casing 20 which is provided with a fluid circuit section 25 (which is described below) causing a medium liquid to circulate in the ultrasonic head unit 10.

For example, the robot arm 2 includes a plurality of arm members 3-*n* (n: a natural number) which are joined rotatably about a plurality of joints. In the Example shown in FIG. 1, the robot arm 2 includes arm members 3-1, 3-2, and 3-3 as the plurality of arm members 3-*n*. The robot arm 2 can rotate around a vertical axis and is installed on a floor surface with an arm pedestal 4 therebetween. The robot arm 2 is constituted to be able to move a holding target to an arbitrary position and hold it in an arbitrary posture state. For example, the robot arm 2 holds the ultrasonic head unit 10 such that an ultrasonic radiation direction is directed toward the patient K who is supported by the therapy bed B below the ultrasonic head unit 10 while the ultrasonic head unit 10 maintains a standing posture.

The ultrasonic head unit 10 has a cylindrical outer shape and is held by the robot arm 2, for example, in a posture in which a central axis TCL of the cylindrical shape lies in an up-down direction. The ultrasonic head unit 10 includes a main body section 11 which includes a holding portion held by the robot arm 2, a contact member 14 which comes into contact with the patient K, and a liquid storage section 12 on which the contact member 14 is mounted and which is constituted to be able to adjust the storage volume thereof in accordance with the amount of medium liquid.

The ultrasonic head unit 10 is constituted to perform therapy by emitting ultrasonic waves to an affected part of the patient K. An ultrasonic-based therapy object may also be applied to animals as well as humans (a therapy object may be an animal other than a human). The ultrasonic head unit 10 includes each of instruments emitting high intensity focused ultrasound (which also hereinafter be referred to as HIFU) that is therapeutic ultrasonic waves and diagnostic ultrasonic waves that are ultrasonic waves different from the HIFU to an affected part inside a therapy object. For example, the ultrasonic head unit 10 includes a wave source 11A, which radiates ultrasonic waves into a therapy object, in a lower side portion on the inward side of the main body section 11 (refer to FIG. 2).

For example, the wave source 11A is provided with a first wave source 11B (refer to FIG. 2) including a diagnostic probe which protrudes from the main body section 11 to an internal space of the liquid storage section 12 and generates diagnostic ultrasonic waves, and a second wave source 11C (refer to FIG. 2) which generates therapeutic HIFU. For example, the first wave source 11B emits diagnostic ultrasonic waves downward from a tip portion (a tip portion of the ultrasonic head unit 10) and receives diagnostic ultrasonic waves reflected by a target such as the body of the patient K. The first wave source 11B emits diagnostic ultrasonic waves in a predetermined angle range with respect to the central axis TCL along the up-down direction and receives reflected waves. The first wave source 11B is provided rotatably around the central axis TCL. The first wave source 11B is provided movably in a direction along the central axis TCL. The first wave source 11B is disposed in the internal space of the liquid storage section 12 covered by the contact member 14.

For example, the second wave source 11C is constituted of a HIFU transducer which generates a plurality of focal points X at equal intervals along the circumference about a central axis that coincides with the central axis TCL. The second wave source 11C includes a radiation surface which is formed to have a dome shape on a lower surface side. For example, the second wave source 11C has a plurality of ultrasonic oscillators (not shown) on the radiation surface. The plurality of ultrasonic oscillators are disposed such that a plurality of oscillated ultrasonic envelope curves are focused at a plurality of focal points. The second wave source 11C is disposed above the first wave source 11B. For example, the second wave source 11C is disposed rotatably about the central axis TCL.

For example, the liquid storage section 12 is constituted to be able to adjust the storage volume inside the liquid storage section 12 by an extensible tubular portion 13 which is constituted of two tubular bodies and the contact member 14 which is provided in a lower portion of the tubular portion 13. The internal space of the liquid storage section 12 is filled with a medium liquid which improves transmissibility of ultrasonic waves. The contact member 14 is constituted to be replaceable as described below.

The contact member 14 is formed to have a bowl shape projecting downward. One surface side (outer side) of the contact member 14 serves as a contact portion which comes into contact with the patient K who is to be a therapy object. The contact portion is a region including a lower end portion of the contact member 14. The other surface side (inner side) of the contact portion is formed to surround an accommodation space which accommodates a medium liquid. Due to the foregoing constitution, while the posture of the ultrasonic head unit 10 is maintained, the robot arm 2 can perform positional setting such that the contact portion of the contact member 14 is brought into contact with the skin which is to be a position on an extended line passing through an affected part of the patient K on the therapy bed B. The casing 20 is disposed adjacent to the robot arm 2.

The casing 20 is provided with the fluid circuit section 25 including a plurality of flow paths which cause a medium liquid to circulate through the ultrasonic head unit 10 as described below. The fluid circuit section 25 supplies a medium liquid to the ultrasonic head unit 10, fills the liquid storage section 12 with a medium liquid, causes a medium liquid to flow out from the liquid storage section 12, and causes a medium liquid to circulate. For example, the fluid circuit section 25 includes pump portions 26 for circulating a medium liquid through the flow paths (refer to FIG. 2), valve portions 27 for stopping circulation of a medium liquid through the flow paths or releasing the stop of circulation (refer to FIG. 2), flow path members Rm for forming liquid flow paths (refer to FIG. 3 described below), and liquid detection portions 28 for detecting a liquid circulating through the flow paths. In addition, the fluid circuit section 25 includes a pressure detection portion 28BB which detects the pressure of a liquid in the liquid storage section 12. In addition, a control device 40 is provided inside the casing 20.

Figure 2:
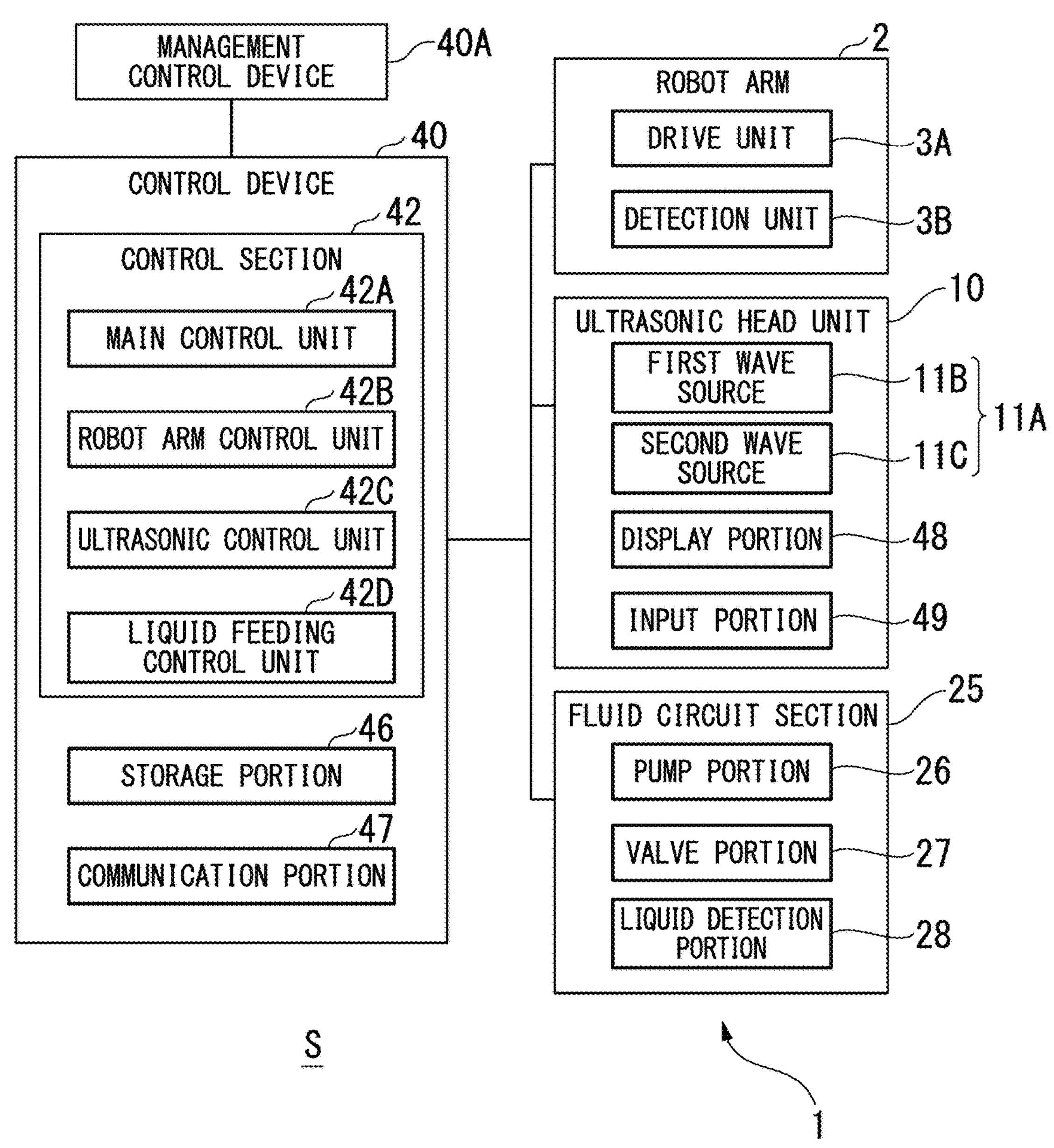
FIG. 2 is a block diagram showing a constitution of the ultrasonic therapy system.

As shown in FIG. 2, the control device 40 is a device for performing control of the ultrasonic therapy device 1 including control of the robot arm 2, control of the ultrasonic head unit 10, and control of the fluid circuit section 25. For example, the control device 40 is constituted of an information processing terminal device such as a personal computer. The control device 40 is connected to the ultrasonic therapy device 1 such that communication can be performed therebetween. The control device 40 may be a device which is directly connected to the ultrasonic therapy device 1 and may also be a server which is connected to a network and connected to the ultrasonic therapy device 1 such that communication can be performed therebetween.

The control device 40 includes a control section 42 which controls the ultrasonic therapy device 1. The control device 40 includes a storage portion 46 which stores data necessary for control, a communication portion 47 which communicates with the ultrasonic therapy device 1, a display portion 48 which displays information necessary for control, and an input portion 49 which receives an operation necessary for control.

The storage portion 46 is a data storage device which is constituted of a storage medium such as a hard disk drive or a flash memory. The storage portion 46 may be built into the control device 40 or may be connected to the outside as an external storage device (may be provided outside the control device 40). The communication portion 47 is a communication interface for transmitting and receiving a control signal between the ultrasonic therapy device 1 and the management control device 40A. The communication portion 47 receives a command signal requesting control, detection signals detected by the robot arm 2, the ultrasonic head unit 10, and the fluid circuit section 25, and the like and transmits control signals for controlling the robot arm 2, the ultrasonic head unit 10, and the fluid circuit section 25. In addition, the communication portion 47 receives a command signal requesting control from the management control device 40A and transmits a detection signal detected by the ultrasonic therapy device 1 and information on the state of work of the ultrasonic head unit 10 to the management control device 40A.

The display portion 48 is constituted of a display device such as a liquid crystal display or an organic electroluminescence (organic EL) display. The input portion 49 is an information input device such as a keyboard or a touch pad. When the display portion 48 is constituted to be able to perform a touch operation, the input portion 49 may be constituted integrally with the display portion 48. The display portion 48 displays a display image including information related to control of the ultrasonic therapy device 1. The display portion 48 displays a diagnostic image of the body of the patient K which is generated based on detection values detected by the first wave source 11B. The display portion 48 is provided in the ultrasonic head unit 10 and is operated by an operator such as a doctor performing therapy.

The control section 42 includes a plurality of control sections for respectively controlling the ultrasonic therapy device 1 as follows. For example, the control section 42 includes a main control unit 42A which comprehensively controls the control of the ultrasonic therapy device 1 based on information input from the input portion 49. For example, the control section 42 includes a robot arm control unit 42B which controls the robot arm 2 based on a command input from the input portion 49. For example, the control section 42 includes an ultrasonic control unit 42C which controls the ultrasonic head unit 10 based on a command input from the input portion 49. For example, the control section 42 includes a liquid feeding control unit 42D which controls the fluid circuit section 25 based on a command input from the input portion 49.

For example, the main control unit 42A generates a command signal for controlling the ultrasonic therapy device 1 based on information input from the input portion 49. The main control unit 42A performs comprehensive control in cooperation with each of the control units described below such that the robot arm 2, the ultrasonic head unit 10, and the fluid circuit section 25 constituted in the ultrasonic therapy device 1 operate in cooperation. For example, the main control unit 42A is constituted of a central processing device provided in the control device 40.

The robot arm control unit 42B controls a drive unit 3A provided in the robot arm 2. For example, the robot arm control unit 42B may be provided on the robot arm 2 side or may be integrated with the control section 42 of the control device 40. For example, the robot arm control unit 42B individually controls a plurality of drive motors provided in the plurality of joints of the robot arm 2. The robot arm control unit 42B acquires a command signal requesting a predetermined operation to the robot arm 2, computes the control amount of each of the plurality of drive motors based on the content of the command signal, and generates a control signal. The robot arm control unit 42B is provided in the drive unit 3A and acquires data from a detection unit 3B which detects the rotation angle, the torque, and the like of each of the drive motors. The robot arm control unit 42B generates a control signal corresponding to the postures of the plurality of arm members 3-*n* and the magnitude and the direction of an applied action force based on data acquired from the detection unit 3B, thereby controlling the robot arm 2.

The robot arm control unit 42B transmits a control signal to the robot arm 2 via the communication portion 47 and performs control such that the robot arm 2 performs a predetermined operation. The robot arm control unit 42B acquires data of the drive amount of each of the joints in the robot arm 2 via the communication portion 47, thereby controlling operation of the robot arm 2.

For example, at the time of therapy, the robot arm control unit 42B controls the robot arm 2 to perform positional setting such that the tip portion of the ultrasonic head unit 10 provided in the robot arm 2 is disposed at the position of an affected part of the patient K and holds the ultrasonic head unit 10 in a predetermined posture. For example, at the time of preparation for therapy before therapy starts, the robot arm control unit 42B controls the robot arm 2 as described below to hold the ultrasonic head unit 10 in a predetermined first posture such that a medium liquid is easily supplied to the liquid storage section 12 of the ultrasonic head unit 10. For example, at the time of preparation for therapy after therapy has ended, the robot arm control unit 42B controls the robot arm 2 as described below to hold the ultrasonic head unit 10 in a predetermined second posture such that a medium liquid is easily discharged from the liquid storage section 12 of the ultrasonic head unit 10.

At the time of therapy, after the ultrasonic head unit 10 is positionally set at a predetermined position, the ultrasonic control unit 42C controls the ultrasonic head unit 10 to perform necessary operation based on an acquired command signal. The ultrasonic control unit 42C may be integrated with the control section 42 of the control device 40. The main control unit 42A acquires a command signal requesting a predetermined operation to the ultrasonic head unit 10 based on an input operation, computes the control amount of each of the plurality of wave sources based on the content of the command signal, generates a control signal, and outputs the control signal to the ultrasonic control unit 42C. The ultrasonic control unit 42C transmits a control signal to the ultrasonic head unit 10 via the communication portion 47 and individually controls the plurality of wave sources. For example, the ultrasonic control unit 42C controls the plurality of wave sources to radiate ultrasonic waves such that the position of an affected part of the patient K and the plurality of focal points X coincide with each other.

The liquid feeding control unit 42D causes a medium liquid to circulate through the flow path members Rm of the fluid circuit section 25 by controlling a circuit control instrument section 21S including a plurality of liquid detection portions 28, a plurality of pump portions 26, and a plurality of valve portions 27 as the control instruments provided in the fluid circuit section 25 as described below. The liquid feeding control unit 42D may be integrated with the control section 42 of the control device 40. The liquid feeding control unit 42D acquires a command signal requesting a predetermined operation to the circuit control instrument section 21S, computes the control amount of each of the control instruments in the circuit control instrument section 21S based on the content of the command signal, and generates a control signal. The liquid feeding control unit 42D transmits a control signal to the circuit control instrument section 21S via the communication portion 47 and performs control such that the circuit control instrument section 21S performs necessary operation.

At the time of therapy, the liquid feeding control unit 42D controls the fluid circuit section 25 to adjust the storage amount of a medium liquid stored in the liquid storage section 12. The storage amount of a medium liquid stored in the liquid storage section 12 is adjusted for adjustment of a storage amount appropriate for transmission of ultrasonic waves from the second wave source 11C which generates therapeutic HIFU. At the time of preparation for therapy before therapy starts, when the ultrasonic head unit 10 is held in the predetermined first posture, the liquid feeding control unit 42D controls the fluid circuit section 25 to supply a new medium liquid to the fluid circuit section 25 and the liquid storage section 12. At the time of preparation for therapy after therapy has ended, when the ultrasonic head unit 10 is held in the predetermined second posture, the liquid feeding control unit 42D controls the fluid circuit section 25 to discharge a medium liquid from the liquid storage section 12 and the fluid circuit section 25. Due to the foregoing constitution, the control device 40 can comprehensively operate the ultrasonic therapy device 1 based on the content of the input operation.

Figure 3:
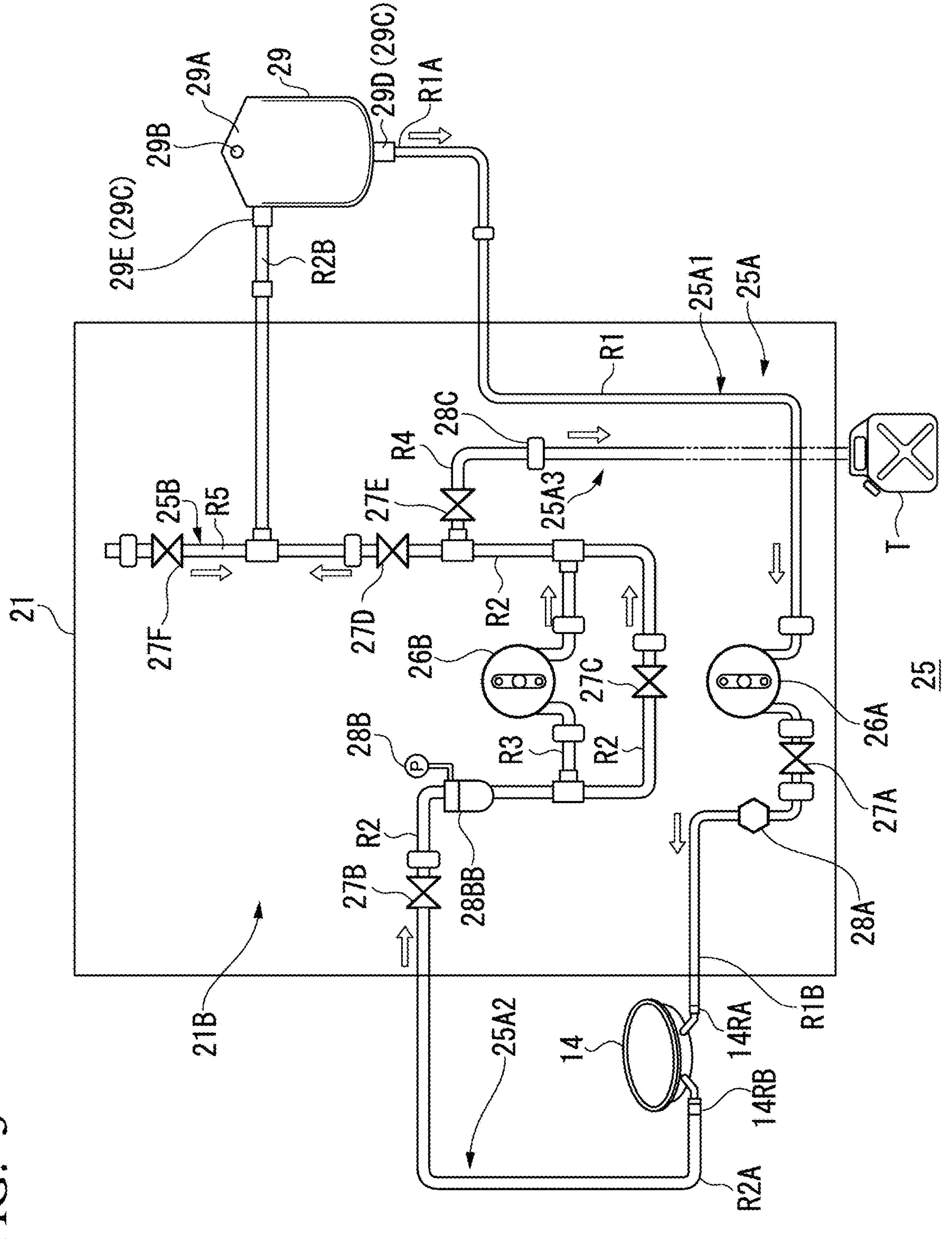
FIG. 3 is a view schematically showing a constitution of a fluid circuit section.

FIG. 3 schematically shows a constitution of the fluid circuit section 25. For example, the fluid circuit section 25 includes a plurality of flow path members Rm (m: a natural number) for circulating a medium liquid, the circuit control instrument section 21S which causes a medium liquid to circulate through the plurality of flow path members Rm, and a liquid container 29 which accommodates a medium liquid. In addition, the fluid circuit section 25 includes an instrument attachment section 21 in which the circuit control instrument section 21S is attached at a predetermined position. The instrument attachment section 21 is described below. The flow path members Rm are constituted to be replaceable for each diagnostic process of the patient K. For example, the flow path members Rm are formed to have a tubular shape using a flexible resin material. For example, the flow path members Rm are formed with polyethylene tubes.

In the Example shown in FIG. 3, the fluid circuit section 25 includes flow path members R1, R2, R3, R4, and R5 as the plurality of flow path members Rm.

For example, the fluid circuit section 25 includes a first circuit portion 25A which causes a medium liquid to circulate through the plurality of flow path members Rm, and a second circuit portion 25B which communicates with outside air and causes gas (air) to flow into the first circuit portion 25A from the outside. For example, the first circuit portion 25A includes an inflow circuit portion 25A1 which causes a medium liquid to flow into the liquid storage section 12, an outflow circuit portion 25A2 which causes a medium liquid to flow out from the liquid storage section 12, and a discharge circuit portion 25A3 which discharges a medium liquid to the outside.

For example, the first circuit portion 25A includes the flow path member R1 which connects the liquid container 29 and the liquid storage section 12 (in FIG. 3, the contact member 14). The liquid storage section 12 (in FIG. 3, the contact member 14) is provided with an inflow connection portion 14RA into which a medium liquid flows, and an outflow connection portion 14RB from which a medium liquid flows out. A terminal end RIB of the flow path member R1 is fitted into the inflow connection portion 14RA in an attachable/detachable manner. For example, the inflow connection portion 14RA is formed with a tubular member using an elastically deformable resin material having a diameter larger than the diameter of the flow path member R1. The inner diameter of the inflow connection portion 14RA is formed to be slightly smaller than the outer diameter of the flow path member R1.

When the flow path member R1 is fitted, the inflow connection portion 14RA is elastically deformed and adheres to the periphery of the terminal end R1B of the flow path member R1 so that airtightness is retained. A start end R2A of the flow path member R2 is fitted into the outflow connection portion 14RB. For example, the outflow connection portion 14RB is formed with a tubular member using an elastically deformable resin material having a diameter larger than the diameter of the flow path member R2. The inner diameter of the outflow connection portion 14RB is formed to be slightly smaller than the outer diameter of the flow path member R2. When the flow path member R2 is fitted, the outflow connection portion 14RB is elastically deformed and adheres to the periphery of the start end R2A of the flow path member R2 so that airtightness is retained. Due to the foregoing constitution, work of connecting the flow path members R1 and R2 in the inflow connection portion 14RA and the outflow connection portion 14RB can be manually performed without requiring any tool. For example, a Luer lock connector can be used for connection between the flow path members R1 and R2 in the inflow connection portion 14RA and the outflow connection portion 14RB. Further, the contact member 14 and the flow path members R1 and R2 can be integrated by being connected via the inflow connection portion 14RA and the outflow connection portion 14RB.

For example, the outflow circuit portion 25A2 includes the flow path member R2 which connects the liquid storage section 12 and the liquid container 29, and the flow path member R3 which bypasses a part in the middle of the flow path member R2. For example, the discharge circuit portion 25A3 includes the flow path member R4 which is connected to a part in the middle of the outflow circuit portion 25A2 and of which the downstream side opens to the outside. For example, a tank T which accommodates a medium liquid is provided on the downstream side of the flow path member R4. The second circuit portion 25B includes the flow path member R5 which branches from the downstream side of the flow path member R2.

For example, the circuit control instrument section 21S (refer to FIGS. 6 and 7, which are described below) is constituted to include the pump portions 26, the valve portions 27, and the liquid detection portions 28 as the control instruments. For example, the pump portions 26 include a liquid supply pump 26A which is provided in the middle of the flow path member R1, and a liquid discharge pump 26B which is provided in the middle of the flow path member R2. The liquid supply pump 26A supplies a medium liquid to the liquid storage section 12 in the inflow circuit portion 25A1. The liquid discharge pump 26B discharges a medium liquid from the liquid storage section 12 in the outflow circuit portion 25A2.

The valve portions 27 include a plurality of electromagnetic valves (pinch valves) 27A to 27F. The liquid detection portions 28 include a concentration meter 28A which is provided in the flow path member R1 and detects the dissolved oxygen concentration inside a medium liquid, a pressure sensor 28B which is provided in the flow path member R2 and included in the pressure detection portion 28BB detecting the pressure inside the flow path members Rm, and a plurality of liquid detection sensors 28C which are respectively provided in the vicinity of the electromagnetic valves 27A to 27F in the flow path members Rm and detect the presence or absence of a medium liquid circulating through the flow path members Rm.

The control section 42 is constituted to be able to release the stop of all the electromagnetic valves 27A to 27F so as to be able to replace the instrument attachment section 21.

The concentration meter 28A is provided between the liquid supply pump 26A and the liquid storage section 12, detects the dissolved oxygen concentration inside a medium liquid supplied to the liquid storage section 12, and monitors the medium liquid necessary for transmission of ultrasonic waves from the second wave source 11C which generates therapeutic HIFU.

The pressure detection portion 28BB is provided between the liquid discharge pump 26B and the liquid storage section 12 and monitors the liquid pressure of a medium liquid flowing through the flow path member R2. The pressure sensor 28B monitors the pressure of a flowing medium liquid by detecting the air pressure in an air pocket formed inside the pressure detection portion 28BB, thereby monitoring the liquid pressure inside the liquid storage section 12. For example, the control section 42 (liquid feeding control unit 42D) performs adjustment of the supply amount of (including stopping supply of) a liquid supplied to the inside of the liquid storage section 12 by controlling the fluid circuit section 25 based on the air pressure of the air pocket detected by the pressure sensor 28B. The supply amount of a liquid supplied to the inside of the liquid storage section 12 is adjusted to prevent the contact member 14 from bursting due to expansion.

In addition, the presence or absence of a liquid and the liquid amount inside the liquid storage section 12 may be monitored by detecting the pressure inside the flow path member R2 using the pressure sensor 28B. For example, based on the pressure inside the flow path member R2 detected by the pressure sensor 28B, the control section 42 (ultrasonic control unit 42C) can control the second wave source 11C which generates therapeutic HIFU, can judge whether or not HIFU can be emitted, and can control operation related to starting or stopping emission of HIFU. What detects the presence or absence of a liquid inside the liquid storage section 12 is not limited to a pressure sensor. For example, a sensor capable of detecting that the inside of the liquid storage section 12 is filled with a liquid and the amount of water necessary for emission of HIFU may be used. In addition, a water amount detection unit using a sensor capable of detecting the amount of water may be constituted.

Figures 4, 5:
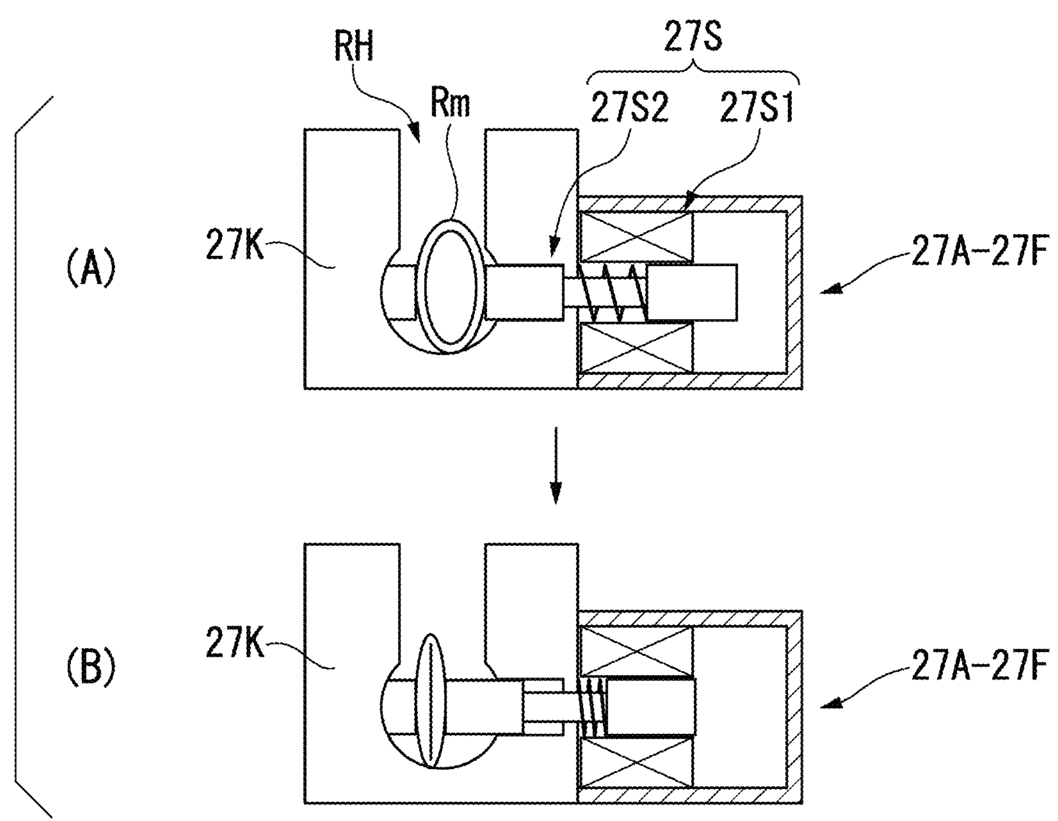
FIG. 4 is a cross-sectional view showing a constitution of an electromagnetic valve.
FIG. 5 is a view showing a constitution of a liquid supply pump and a liquid discharge pump.

As shown in FIG. 4, for example, the electromagnetic valves 27A to 27F are constituted of a clamp portion 27K which clamps the flow path member Rm, and a solenoid actuator 27S which is provided in the clamp portion 27K. The flow path member Rm is mounted in the clamp portion 27K serving as a flow path holding portion RH. In the clamp portion 27K, the flow path member Rm is clamped in an attachable/detachable manner with respect to the clamping position of the clamp portion 27K. The clamp portion 27K opens outward on a side surface of the casing 20, and the flow path member Rm passes through the opening of the clamp portion 27K and is constituted in an attachable/detachable manner at the clamping position of the clamp portion 27K. The solenoid actuator 27S includes an electromagnetic coil 27S1 and a plunger 27S2 which slides with respect to the electromagnetic coil 27S1 (refer to FIG. 4(A)). When the electromagnetic coil 27S1 is electrified, the plunger 27S2 moves in a direction in which it protrudes to the inner side of the clamp portion 27K (refer to FIG. 4(B)). At this time, the plunger 27S2 squashes the flow path member Rm in cooperation with the clamp portion 27K and stops a flow of a medium liquid circulating inside the flow path member Rm.

Returning to FIG. 3, for example, the electromagnetic valve 27A is provided on the downstream side part of the liquid supply pump 26A in the flow path member R1. The electromagnetic valve 27A causes a medium liquid in the flow path member R1 to flow or stop (stops a flow or releases the stop). For example, the electromagnetic valve 27B is provided on the downstream side of the liquid storage section 12 in the flow path member R2. The electromagnetic valve 27B causes a medium liquid in the flow path member R2 to flow or stop. For example, the electromagnetic valve 27C is provided in a part in the flow path member R2 extending parallel to the flow path member R3. The electromagnetic valve 27C causes a medium liquid in the flow path member R2 to flow or stop at the time of filling or at the time of discharging a medium liquid.

For example, the electromagnetic valve 27D is provided on the upstream side of the liquid container 29 in the downstream side part of the flow path member R2. For example, the electromagnetic valve 27D causes a medium liquid in the flow path member R2 to flow or stop at the time of circulating and at the time of filling a medium liquid. The electromagnetic valve 27E is provided in the flow path member R4. The electromagnetic valve 27E causes a medium liquid in the flow path member R4 to flow or stop at the time of discharging a medium liquid. For example, the electromagnetic valve 27F is provided in the flow path member R5. The electromagnetic valve 27F causes air to flow at the time of flowing from the flow path member R5 to the inside of the first circuit portion 25A or stop the flow.

As shown in FIG. 5, for example, the liquid supply pump 26A is constituted of a tube pump which pressure-feeds a medium liquid in the flow path member R1 by causing a cross-sectional shape of the flow path member of the flow path member R1 to be continuously deformed from one side to the other side in a flowing direction. The liquid supply pump 26A includes a rotation roller 26A1, and a housing 26A2 which rotatably supports the rotation roller 26A1. The liquid supply pump 26A includes the rotation roller 26A1 and the housing 26A2 as a flow path holding portion RJ in which the flow path member Rm is mounted, and the flow path member Rm is mounted between the rotation roller 26A1 and the housing 26A2. The rotation roller 26A1 is constituted such that an end portion of the rotation roller 26A1 can move in a radiation direction from a rotation center of the rotation roller 26A1. In addition, the end portion of the rotation roller 26A1 includes a biasing member (not shown) which applies a predetermined biasing force in a direction separated from the rotation center. A gap is provided with respect to the housing 26A2 by moving the end portion of the rotation roller 26A1 in the direction toward the rotation center against a biasing force of the biasing member. The flow path member R1 is fitted into the gap. The flow path member R1 is clamped, squashed, and deformed by an inner wall of the housing 26A2 and the end portion of the rotation roller 26A1, thereby being mounted in the flow path holding portion RJ.

In the liquid supply pump 26A, if the rotation roller 26A1 is rotated, the end portion of the rotation roller 26A1 moves while squashing the flow path member R1 in the rotation direction, and a medium liquid inside the flow path member R1 is pressure-fed to the downstream side in the rotation direction. After the rotation roller 26A1 has moved, the squashed flow path member R1 returns to the original shape due to the restoring force of the flow path member itself. At this time, a medium liquid flows in the flow path member R1 from the upstream side of the flow path member R1. Similar to the liquid supply pump 26A, the liquid discharge pump 26B is also constituted of a tube pump.

For example, part of the flow path member R1 is fitted into the liquid supply pump 26A in a curved state in an attachable/detachable manner. For example, part of the flow path member R3 is fitted into the liquid discharge pump 26B in a curved state in an attachable/detachable manner. Due to the foregoing constitution, work of attaching and detaching the flow path members R1 and R3 in the liquid supply pump 26A and the liquid discharge pump 26B can be manually performed without requiring any tool.

Returning to FIG. 3, the liquid container 29 is formed into a bag using a resin material such as polyethylene or polypropylene. The liquid container 29 is formed by welding peripheral parts of two sheet-shaped resin materials. An upper portion of the liquid container 29 is provided with a bonding portion 29A in which two sheet-shaped resin materials are bonded together over a predetermined width. An upper portion of the bonding portion 29A is provided with an engagement portion 29B which is formed as a penetration hole. A hook-shaped support member 24 of a support portion 23 provided on the casing 20 as described below engages with the engagement portion 29B, and the liquid container 29 is held in a suspended state.

A medium liquid is sealed inside the liquid container 29 in a state of having no air bubbles. The medium liquid is degassed water from which dissolved gas is removed in order to improve conductivity of ultrasonic waves. Regarding the degassed water used as a medium liquid in the present Example, degassed water having a value of dissolved gas (dissolved oxygen concentration value) contained in the liquid equal to or smaller than a predetermined value (3 ppm) is used. The liquid container 29 is prepared in a state in which a medium liquid is accommodated inside the accommodation space thereof and connected to the fluid circuit section 25 so that the medium liquid can be supplied to the fluid circuit section 25.

The liquid container 29 is provided with a connection portion 29C for connection to the fluid circuit section 25. The connection portion 29C includes a first connection portion 29D which is connected to the inflow circuit portion 25A1 in order to supply a medium liquid, and a second connection portion 29E which is connected to the outflow circuit portion 25A2 for returning a medium liquid from the liquid storage section 12 (in FIG. 3, the contact member 14) to the liquid container 29. For example, the first connection portion 29D is provided in a lower portion of the liquid container 29 in a suspended manner.

A start end R1A of the flow path member R1 is fitted into the first connection portion 29D in an attachable/detachable manner. For example, the first connection portion 29D is formed with a tubular member using an elastically deformable resin material having a diameter larger than the diameter of the flow path member R1. The inner diameter of the first connection portion 29D is formed to be slightly smaller than the outer diameter of the flow path member R1. When the flow path member R1 is fitted, the first connection portion 29D is elastically deformed and adheres to the periphery of the start end R1A of the flow path member R1 so that airtightness is retained. As the first connection portion 29D, a Luer lock connector may be used as a general medical care member.

For example, the second connection portion 29E is provided in the upper portion of the liquid container 29 in a manner of protruding in a horizontal direction. A terminal end R2B of the flow path member R2 is fitted into the second connection portion 29E in an attachable/detachable manner. For example, the second connection portion 29E is formed with a tubular member using an elastically deformable resin material having a diameter larger than the diameter of the flow path member R2. The inner diameter of the second connection portion 29E is formed to be slightly smaller than the outer diameter of the flow path member R2. When the flow path member R2 is fitted, the second connection portion 29E is elastically deformed and adheres to a periphery of the terminal end R2B of the flow path member R2 so that airtightness is retained. As the second connection portion 29E, a Luer lock connector may be used as a general medical care member.

A medium liquid unit 29UT is constituted to include the liquid container 29, the connection portion 29C, and the engagement portion 29B. Due to the foregoing constitution, work of connecting the flow path members R1 and R2 and the liquid container 29 can be manually performed without requiring any tool. Further, the liquid container 29 and the flow path members R1 and R2 can be integrated by being connected via the connection portion 29C.

Figure 6:
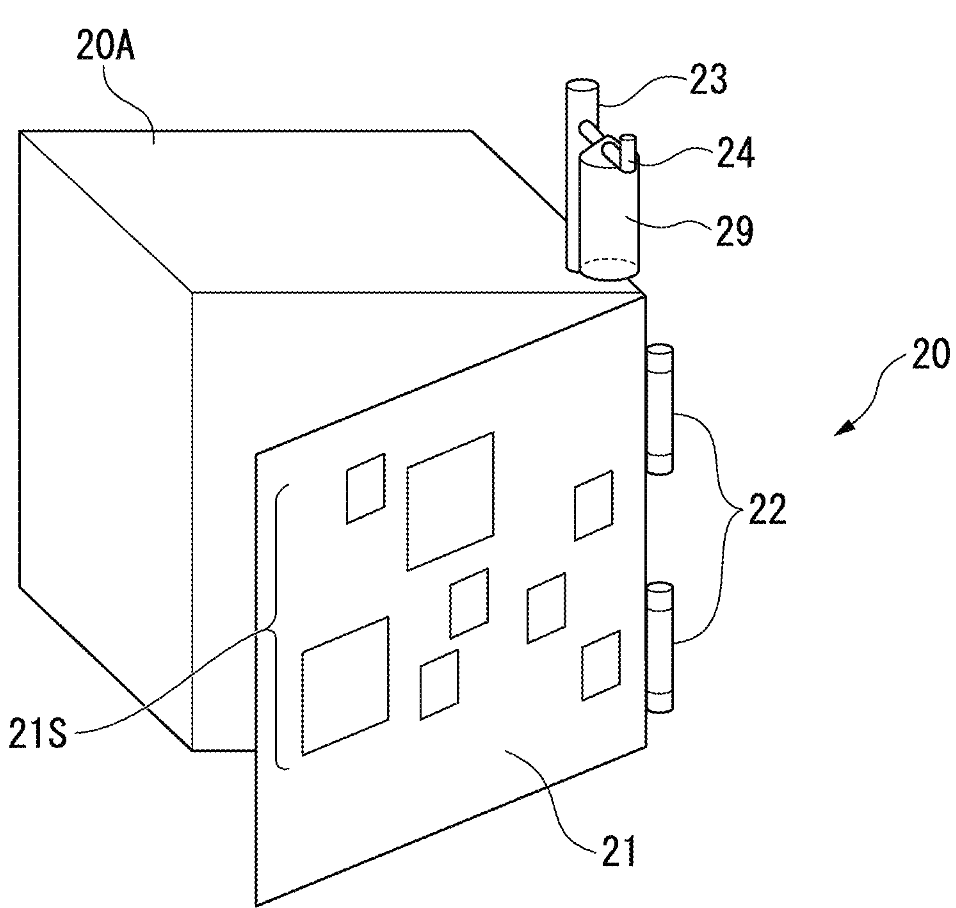
FIG. 6 is a perspective view showing a constitution of an instrument attachment section provided in a casing.

As shown in FIG. 6, the casing 20 is provided with the instrument attachment section 21 to which the fluid circuit section 25 is attached such that one surface side of the fluid circuit section 25 faces the outside. For example, in the instrument attachment section 21, the flow path holding portions RH and RJ (which are described below) are provided side by side on one side surface of the casing 20. The instrument attachment section 21 is rotatably supported by rotation support portions 22 which are provided along one side extending in the up-down direction of the casing 20. The instrument attachment section 21 is provided in a door shape which can be opened and closed with respect to a casing main body 20A.

The support portion 23, which is formed to have a rod shape supporting the liquid container 29, is provided on an upper surface of the casing 20. The hook-shaped support member 24, with which the engagement portion 29B provided in the liquid container 29 engages, is provided in an upper portion of the support portion 23. In the support portion 23, the liquid container 29 is suspended when the engagement portion 29B engages with the support member 24.

Figure 7:
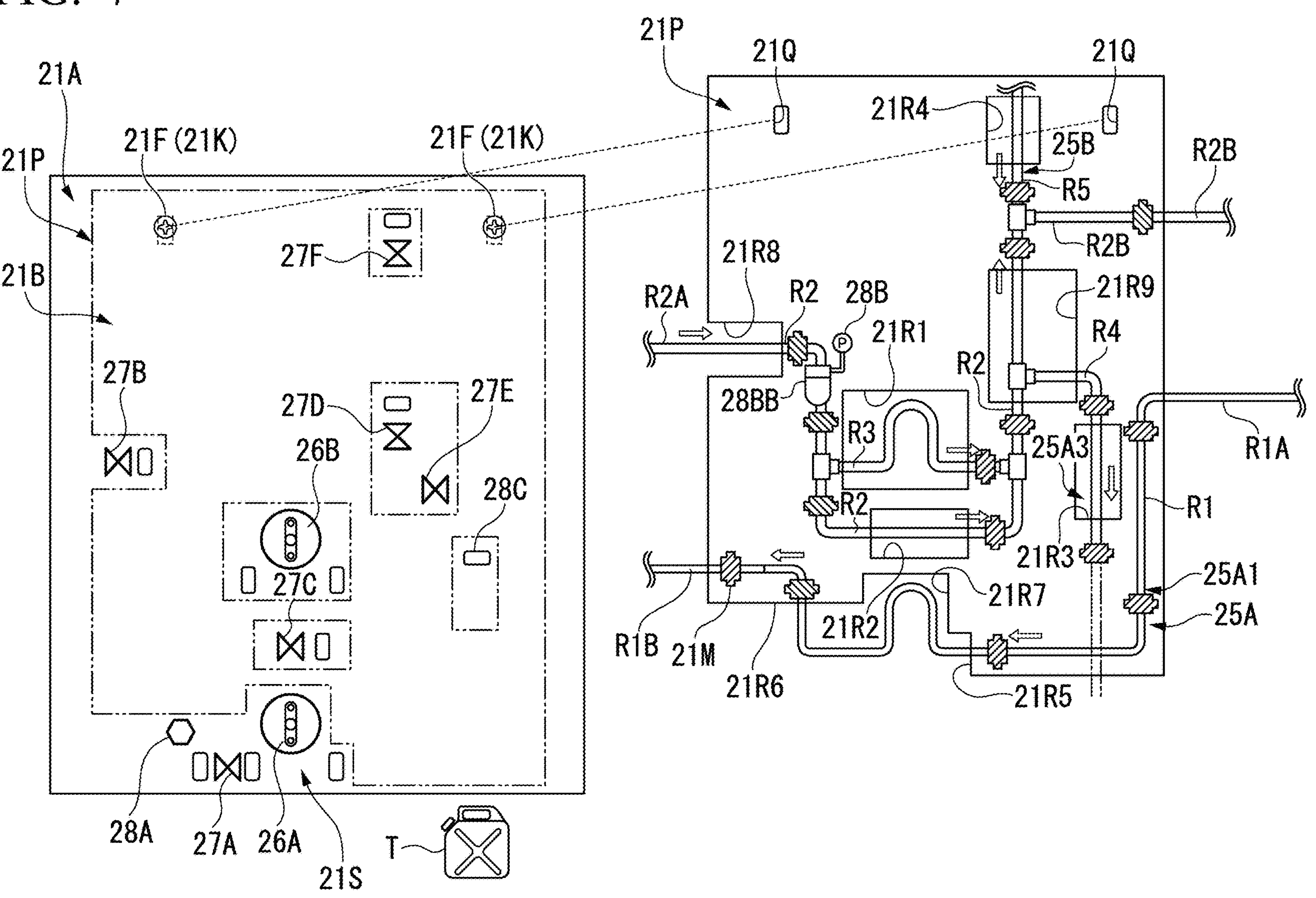
FIG. 7 is a view showing a constitution of the fluid circuit section.

As shown in FIG. 7, part of the fluid circuit section 25 is provided in the instrument attachment section 21. The instrument attachment section 21 includes a first attachment portion 21A. The circuit control instrument section 21S is provided in the first attachment portion 21A. The circuit control instrument section 21S is used for controlling a flow of a medium liquid circulating through the plurality of flow path members Rm. In addition, the instrument attachment section 21 includes a second attachment portion 21B to which the plurality of flow path members Rm are attached. The control instruments in the circuit control instrument section 21S causing a medium liquid to circulate through the plurality of flow path members Rm are attached to one surface side of the instrument attachment section 21 facing outward. The liquid supply pump 26A, the liquid discharge pump 26B, the plurality of electromagnetic valves 27A to 27F, and the plurality of liquid detection sensors 28C are attached to the one surface side of the instrument attachment section 21 at predetermined positions as the control instruments constituting the circuit control instrument section 21S. Accordingly, the one surface side of the instrument attachment section 21 constitutes the first attachment portion 21A.

The second attachment portion 21B is provided correspondingly to the first attachment portion 21A on the one surface side of the instrument attachment section 21 in an attachable/detachable manner. The circuit control instrument section 21S is disposed on one surface side of the first attachment portion 21A facing outward. The flow path holding portions RH and RJ holding the respective flow path members Rm are disposed by disposing the control instruments in the circuit control instrument section 21S (refer to FIGS. 4 and 5). A plurality of flow path support portions 21M are disposed on one surface side of the second attachment portion 21B facing outward. The flow path members Rm are respectively attached to the plurality of flow path support portions 21M.

For example, the second attachment portion 21B includes a detachable attachment member 21P which is formed to have a plate shape, and the plurality of flow path members Rm which are provided in the detachable attachment member 21P. On one surface side of the detachable attachment member 21P facing outward, the plurality of flow path members Rm are disposed in advance at predetermined positions. The plurality of flow path members Rm are attached at the predetermined positions based on a disposition relationship set in advance. Before the detachable attachment member 21P is mounted on the first attachment portion 21A (before the start end R1A of the flow path member R1 and the terminal end R2B of the flow path member R2 are connected to the liquid container 29), the plurality of flow path members Rm are attached to the detachable attachment member 21P in a state in which the start end R1A of the flow path member R1 and the terminal end R2B of the flow path member R2 open. The start end R1A of the flow path member R1 and the terminal end R2B of the flow path member R2 are connected to the liquid container 29 when the liquid container 29 is attached to the support portion 23 (refer to FIG. 3).

Before the detachable attachment member 21P is mounted on the first attachment portion 21A (before the terminal end R1B of the flow path member R1 and the start end R2A of the flow path member R2 are connected to the liquid storage section 12), the plurality of flow path members Rm are attached to the detachable attachment member 21P in a state in which the terminal end R1B of the flow path member R1 and the start end R2A of the flow path member R2 open outward. The terminal end R1B of the flow path member R1 and the start end R2A of the flow path member R2 are connected to the liquid storage section 12. In the present Example, the terminal end R1B of the flow path member R1 and the start end R2A of the flow path member R2 are connected to the contact member 14. In the detachable attachment member 21P, the plurality of flow path members Rm are positionally set and attached in a state of being exposed at a plurality of predetermined positions. For example, the plurality of predetermined positions are positions corresponding to the positions of the control instruments included in the circuit control instrument section 21S provided on the instrument attachment section 21.

For example, at least some of the plurality of flow path support portions 21M are disposed at positions on the upstream side and the downstream side of the positions of the control instruments included in the circuit control instrument section 21S in the circulation direction in which a medium liquid circulates through the flow path members Rm.

The second attachment portion 21B is provided in an attachable/detachable manner with respect to the first attachment portion 21A. The plurality of flow path members Rm are disposed in the second attachment portion 21B. The plurality of flow path members Rm are disposed correspondingly to the position of the circuit control instrument section 21S disposed in the first attachment portion 21A. Detachable engagement portions 21K, which cause the detachable attachment member 21P to be positionally set at a predetermined position and engage with the first attachment portion 21A, are provided on the one surface side of the instrument attachment section 21.

For example, the detachable engagement portions 21K are formed with one or more hook members 21F. A pair of hook members 21F are attached to an upper part on the one surface side of the instrument attachment section 21. A pair of mounting engagement portions 21Q with which the hooks of the pair of hook members 21F respectively engage are formed on the detachable attachment member 21P. The mounting engagement portions 21Q are formed as penetration holes. For example, the pair of mounting engagement portions 21Q are formed correspondingly to the respective positions of the hooks of the pair of hook members 21F. The penetration holes formed as the mounting engagement portions 21Q are formed in an upper end portion of the detachable attachment member 21P. The mounting engagement portions 21Q are formed as openings having a vertically elongated rectangular shape such that the upper ends of the mounting engagement portions 21Q can be hooked onto the hooks after the hooks of the hook members 21F penetrate the openings.

Accordingly, the second attachment portion 21B is exactly positionally set and attached to the first attachment portion 21A. As a result, the control instruments in the circuit control instrument section 21S disposed on the first attachment portion 21A and the plurality of flow path members Rm provided on the second attachment portion 21B can be positionally set correspondingly. At this time, the second attachment portion 21B can be manually attached to the first attachment portion 21A without requiring any tool. When the second attachment portion 21B is attached, the plurality of exposed flow path members Rm are attached to the control instruments in the circuit control instrument section 21S. In the detachable attachment member 21P, cutout portions 21Ro (o: a natural number), which are formed by cutting out part of the plate-shaped detachable attachment member 21P in a predetermined size, are provided. The cutout portions 21Ro are formed as necessary at positions corresponding to the positions of the control instruments in the circuit control instrument section 21S. In the present Example, a plurality of cutout portions 21Ro (21R1 to 21R9) are formed.

In the plurality of cutout portions 21Ro in the detachable attachment member 21P, the plurality of flow path members Rm are positionally set and attached in an exposed state while retaining a predetermined piping posture state at predetermined positions. For example, the first cutout portion 21R1 is provided at a position in the detachable attachment member 21P corresponding to the position of the liquid discharge pump 26B. The first cutout portion 21R1 is formed to have a size and a shape so as not to come into contact with the liquid discharge pump 26B when the detachable attachment member 21P is attached or detached with respect to the instrument attachment section 21. The flow path member R3 is attached in a state of being exposed through the first cutout portion 21R1.

The flow path member R3 is exposed in a loop shape in the first cutout portion 21R1 such that the detachable attachment member 21P matches the mounting position of the housing of the liquid discharge pump 26B and is easily attached and detached when the detachable attachment member 21P is attached on and detached from the one surface side of the instrument attachment section 21. The second cutout portion 21R2 is provided at a position in the detachable attachment member 21P corresponding to the positions of the electromagnetic valve 27C and one of the plurality of liquid detection sensors 28C, and part of the flow path member R2 and the flow path member R3 is exposed through the second cutout portion 21R2. The third cutout portion 21R3 is provided at a position in the detachable attachment member 21P corresponding to the position of the liquid detection sensor 28C which is disposed on the downstream side of the electromagnetic valve 27E. Part of the flow path member R4 is exposed through the third cutout portion 21R3, and a terminal end R4E of the flow path member R4 opens.

The fourth cutout portion 21R4 is provided at a position in the detachable attachment member 21P corresponding to the positions of the electromagnetic valve 27F and the liquid detection sensor 28C, and part of the flow path member R5 is exposed through the fourth cutout portion 21R4. The fifth cutout portion 21R5 is provided at a position in the detachable attachment member 21P corresponding to the position of the liquid detection sensor 28C, and part of the flow path member R1 is exposed through the fifth cutout portion 21R5. The sixth cutout portion 21R6 is provided at a position in the detachable attachment member 21P corresponding to the positions of the electromagnetic valve 27A and the liquid detection sensor 28C, and part of the flow path member R1 is exposed through the sixth cutout portion 21R6. The seventh cutout portion 21R7 is provided at a position in the detachable attachment member 21P corresponding to the positions of the liquid supply pump 26A and the liquid detection sensor 28C, and part of the flow path member R1 is exposed in a loop shape through the seventh cutout portion 21R7. The eighth cutout portion 21R8 is provided at a position in the detachable attachment member 21P corresponding to the position of the electromagnetic valve 27B, and part of the flow path member R2 is exposed through the eighth cutout portion 21R8. The ninth cutout portion 21R9 is provided at a position in the detachable attachment member 21P corresponding to the positions of the electromagnetic valve 27D, the liquid detection sensor 28C, and the electromagnetic valve 27E, and part of the flow path member R2 is exposed through the ninth cutout portion 21R9.

Due to the foregoing constitution, when the second attachment portion 21B is attached to the first attachment portion 21A, the plurality of exposed flow path members Rm are attached in a manner of being held by the corresponding control instruments of the circuit control instrument section 21S via the cutout portions 21Ro which are formed as necessary. The circuit control instrument section 21S constitutes the plurality of flow path holding portions RH and RJ which are provided on the first attachment portion 21A and respectively hold the plurality of flow path members Rm.

Due to the foregoing constitution, work of attaching and detaching the plurality of exposed flow path members Rm can be manually performed via the plurality of cutout portions 21Ro with respect to the flow path holding portions RH and RJ respectively provided in the pump portions 26, the valve portions 27, and the liquid detection portions 28 as the control instruments constituting the circuit control instrument section 21S.

Figure 8:
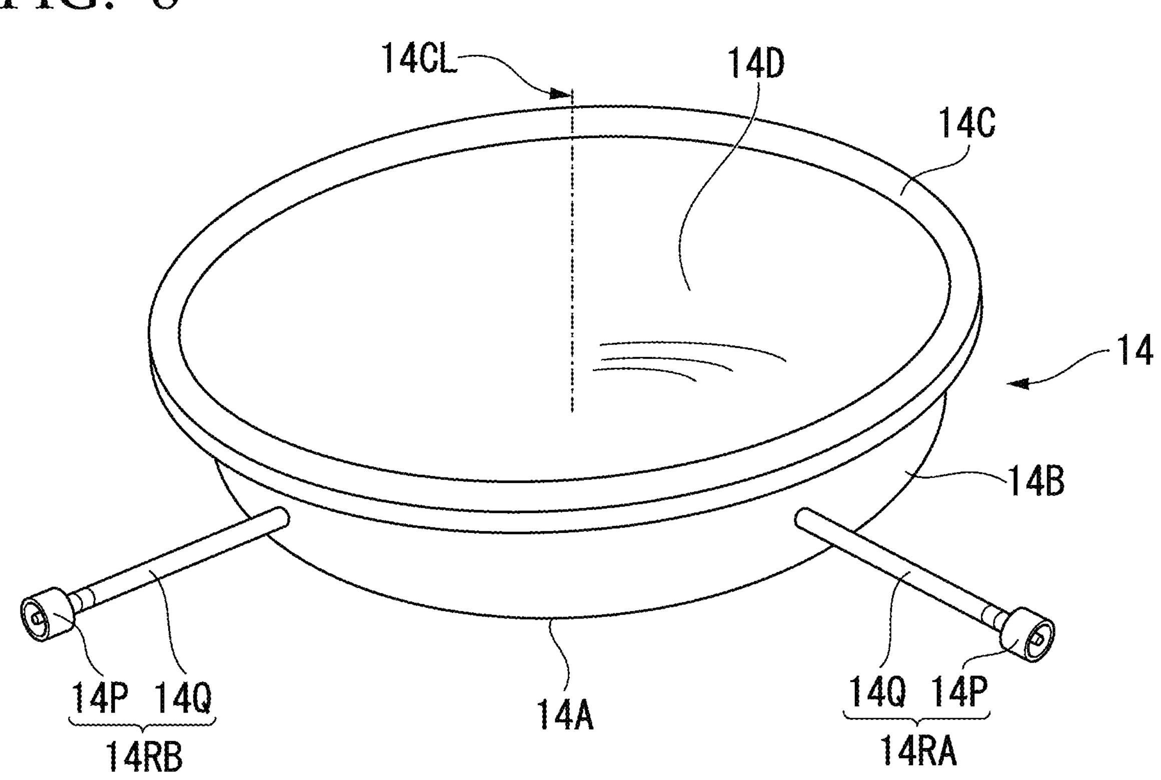
FIG. 8 is a perspective view showing a constitution of a contact member.

As shown in FIG. 8, the contact member 14 provided on the liquid storage section 12 is formed in a bowl shape projecting downward (toward patient side). The contact member 14 is formed of a material which is biocompatible and has an acoustic impedance close to that of a living body. For example, the contact member 14 is formed of a flexible material such as silicon rubber. The liquid storage section 12 side of the contact member 14 that is a side opposite to the patient side is filled with a medium liquid. The contact member 14 is formed to be replaceable for each therapy. A contact portion 14A which comes into contact with the body of the patient K is formed on the lower surface side of the contact member 14 that is the patient side. The contact portion 14A is formed to have a circular bowl shape. A tubular mounting portion 14B, of which the lower portion is connected to the contact portion 14A and which extends in a manner of surrounding an upper part around the contact portion 14A, is formed around the contact portion 14A. For example, the mounting portion 14B is formed to have a circular truncated cone shape with a diameter increasing upward. The mounting portion 14B is mounted on a mounting target part (not shown) of the ultrasonic head unit 10. A flange portion 14C which engages with the mounting target part is formed at an upper end of the mounting portion 14B. The flange portion 14C is formed to have a ring shape protruding outward in the horizontal direction.

For example, part of the internal space is formed by the contact portion 14A and the mounting portion 14B on the inward side of the liquid storage section 12. The internal space is filled with a medium liquid. The inflow connection portion 14RA which is connected to the inflow circuit portion 25A1 is provided at a first position on the mounting portion 14B.

The inflow connection portion 14RA is connected to the flow path member R1 and causes a medium liquid to flow into the contact member 14. The inflow connection portion 14RA constitutes a tubular portion 14Q of which one end side is connected to the mounting portion 14B, and a connection member 14P which is provided on the other end side of the tubular portion 14Q. The terminal end R1B of the flow path member R1 is fitted into the connection member 14P. The outflow connection portion 14RB which is connected to the inflow circuit portion 25A1 is provided at a second position different from the first position on the mounting portion 14B in a plan view. For example, the second position is a position which is shifted in phase from the first position by 90 degrees about a center 14CL of the contact portion 14A in a plan view. The outflow connection portion 14RB is connected to the flow path member R2 and causes a medium liquid to flow out from the contact member 14.

The outflow connection portion 14RB includes the tubular portion 14Q of which one end side is connected to the mounting portion 14B, and the connection member 14P which is provided on the other end side of the tubular portion 14Q. The start end R2A of the flow path member R2 is fitted into the connection member 14P.

Due to the foregoing constitution, work of connecting the inflow connection portion 14RA and the outflow connection portion 14RB to the flow path members R1 and R2 can be manually performed without requiring any tool. For example, a Luer lock connector which is generally utilized as a medical care instrument member is used as the connection member 14P. In addition, it is preferable that the positions in the mounting portion 14B where the inflow connection portion 14RA and the outflow connection portion 14RB are provided be positions close to the flange portion 14C.

After attachment of the plurality of flow path members Rm of the fluid circuit section 25 is completed, the control section 42 controls the liquid supply pump 26A and the electromagnetic valves 27A to 27F to supply a medium liquid to the flow path members Rm and to supply a medium liquid to the liquid storage section 12.

When the plurality of flow path members Rm of the fluid circuit section 25 are detached (specifically, before the plurality of flow path members Rm are detached), the control section 42 controls the liquid supply pump 26A, the liquid discharge pump 26B, and the electromagnetic valves 27A to 27F to discharge a medium liquid from the flow path members Rm and to discharge a medium liquid from the liquid storage section 12. At the time of preparation for therapy, the control section 42 controls the robot arm 2 to maintain the ultrasonic head unit 10 in a posture for liquid supply or a posture for liquid discharge such that a medium liquid is easily supplied to the liquid storage section 12 or discharged from the liquid storage section 12.

In replacement work in which the flow path members Rm of the fluid circuit section 25 are attached, the control section 42 controls the robot arm 2 to move the ultrasonic head unit 10 to a replacement work position that is a predetermined position with respect to the fluid circuit section 25 and adjust the posture of the liquid storage section 12 such that a medium liquid is easily supplied to the liquid storage section 12. In replacement work in which the flow path members Rm of the fluid circuit section 25 are detached, the control section 42 controls the robot arm 2 to move the ultrasonic head unit 10 to the replacement work position that is a predetermined position with respect to the fluid circuit section 25 and adjust the posture of the liquid storage section 12 such that a medium liquid is easily discharged from the liquid storage section 12. For example, a position around the fluid circuit section 25 is set as the replacement work position. Regarding a specific replacement work position, a position separated upward from the upper surface of the casing 20 where the fluid circuit section 25 is provided is set.

Figure 9:
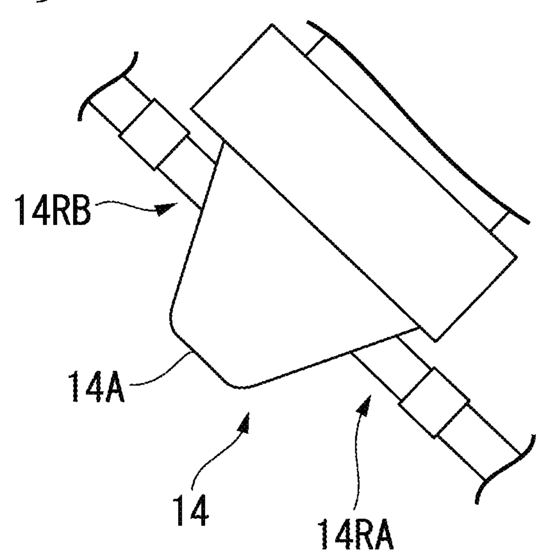
FIG. 9 is a view showing a first posture when a medium liquid is supplied to the contact member.

As shown in FIG. 9, in a liquid supplying step at the time of preparation for therapy, the control section 42 controls the robot arm 2 to hold the ultrasonic head unit 10 in the first posture. For example, the first posture is a posture in which the outflow connection portion 14RB is located on a side higher than the inflow connection portion 14RA such that air inside the liquid storage section 12 is likely to be released. In the present Example, the first posture is a posture in which the contact portion 14A of the contact member 14 (liquid storage section 12) faces the lower side. The first posture is preferably a posture in which the outflow connection portion 14RB becomes the uppermost portion in the liquid storage section 12. The control section 42 controls the circuit control instrument section 21S of the fluid circuit section 25 in a state in which the ultrasonic head unit 10 is held in the first posture to supply a medium liquid to the contact member 14 (liquid storage section 12).

Figure 10:
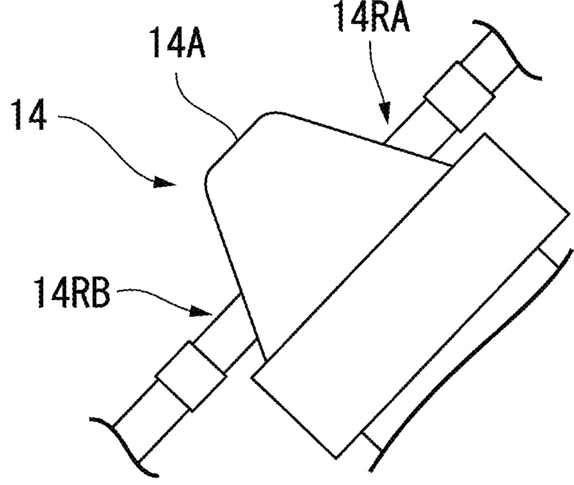
FIG. 10 is a view showing a second posture when a medium liquid is discharged from the contact member.

As shown in FIG. 10, in a liquid discharging step at the time of preparation for therapy, the control section 42 controls the robot arm 2 to hold the ultrasonic head unit 10 in the second posture. For example, the second posture is a posture in which the outflow connection portion 14RB is located on a side lower than the inflow connection portion 14RA such that a medium liquid inside the liquid storage section 12 is likely to be released. In the present Example, since the contact portion 14A of the contact member 14 (liquid storage section 12) is in a posture facing the upper side, replacement of the contact member 14 after liquid discharge can be performed efficiently and easily. The second posture is preferably a posture in which the outflow connection portion 14RB becomes the lowermost portion in the liquid storage section 12. The control section 42 controls the circuit control instrument section 21S of the fluid circuit section 25 in a state in which the ultrasonic head unit 10 is held in the second posture to discharge a medium liquid from the contact member 14 (liquid storage section 12).

Figure 11:
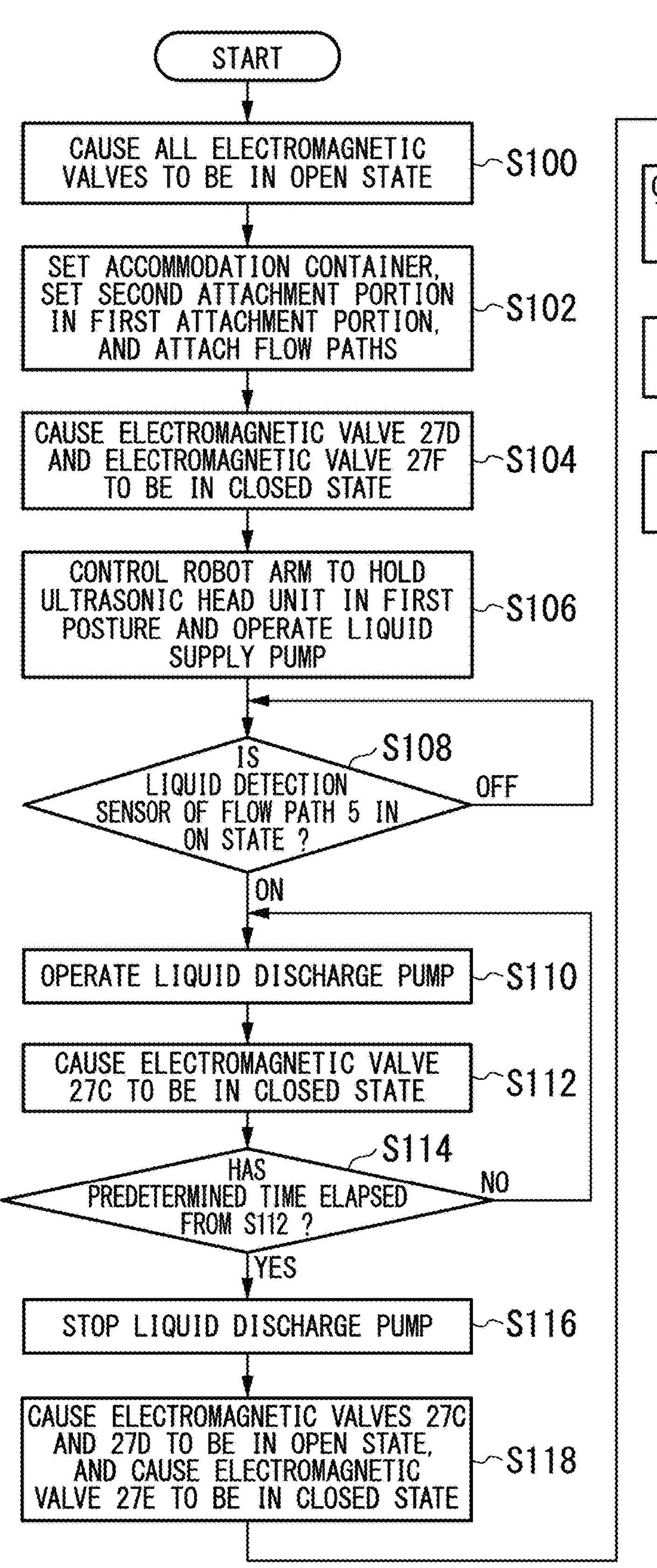
FIG. 11 is a flowchart showing a flow of processing executed in a liquid supplying step at the time of preparation for therapy.
Figure 11:
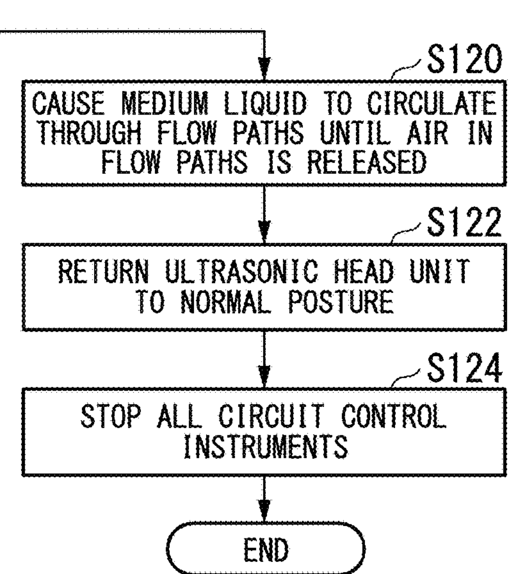

FIG. 11 shows a flowchart of a flow of processing executed in the liquid supplying step at the time of preparation for therapy. A worker inputs an operation of starting attachment of the flow path members Rm of the fluid circuit section 25 using the input portion 49 of the control device 40. The control section 42 controls the robot arm 2 to move the ultrasonic head unit 10 to a position suitable for replacement work based on an input command signal for starting replacement. The control section 42 causes all the electromagnetic valves 27A to 27F to be in an open state (Step S100). The worker sets the contact member 14 in the tubular portion 13, sets the liquid container 29 in the support portion 23 of the casing 20, sets the second attachment portion 21B on which the plurality of flow path members Rm are provided on the first attachment portion 21A, and attaches the plurality of flow path members Rm to the control instruments in the circuit control instrument section 21S. At this time, the worker connects the plurality of flow path members Rm to the liquid container 29 and the liquid storage section 12 (contact member 14) (Step S102).

The control section 42 causes the electromagnetic valve 27D which is provided on the downstream side of the flow path member R2 and the electromagnetic valve 27F which is provided in the flow path member R5 to be in a closed state (Step S104). Accordingly, a medium liquid circulates through the flow path member R1 to the flow path member R3 and then is discharged from the flow path member R4. In response to the input through the input portion 49 of the control device 40, the control section 42 controls the robot arm 2 to hold the ultrasonic head unit 10 in the first posture and operate the liquid supply pump 26A (Step S106). The control section 42 monitors whether or not the liquid detection sensor 28C provided in the flow path member R4 is in an ON state (Step S108), and Step S106 continues when the liquid detection sensor 28C is in an OFF state. When the liquid detection sensor 28C provided in the flow path member R4 is in the ON state, the control section 42 operates the liquid discharge pump 26B (Step S110). When a medium liquid circulates through the flow path member R4, it is a state in which a medium liquid circulates through the flow path members R1 to R3 of the inflow circuit portion 25A1 and the outflow circuit portion 25A2. Therefore, when the liquid detection sensor 28C provided in the flow path member R4 is in the ON state, the control section 42 operates the liquid discharge pump 26B and causes the medium liquid to circulate through the downstream side of the flow path member R2.

The control section 42 causes the electromagnetic valve 27C provided in the flow path members Rm to be in the closed state (Step S112). After Step S112, the control section 42 operates the liquid discharge pump 26B for a predetermined time such as three seconds, for example (Step S114). Before an elapse of the predetermined time, the processing returns to Step S110, and when the predetermined time has elapsed, the liquid discharge pump 26B is stopped (Step S116). Accordingly, air on the downstream side of the flow path member R2 can be released. The control section 42 causes the electromagnetic valve 27C which is provided in the flow path member R2 parallel to the flow path member R3 and the electromagnetic valve 27D which is provided on the downstream side of the flow path member R2 to be in the open state and causes the electromagnetic valve 27E provided in the flow path member R4 to be in the closed state (Step S118).

The control section 42 continues to operate the liquid supply pump 26A and causes the medium liquid to circulate through the flow path members Rm and the liquid container 29 (Step S120). At this time, the worker checks whether or not there are any air bubbles inside the flow path members Rm and the liquid storage section 12. When there are air bubbles which have adhered to an inner surface thereof, the worker strikes the flow path members Rm and the contact member 14 to apply vibration and removes the air bubbles. The control section 42 controls the robot arm 2 to return the ultrasonic head unit 10 to a normal posture (liquid supply completion position) (Step S122). The control section 42 stops the liquid supply pump 26A and stops all the corresponding circuit control instrument section 21S (Step S124). Each of the foregoing steps may be automatically performed by the control section 42, and it may be suitably stopped or started based on an operation input from the input portion 49.

Figure 12:
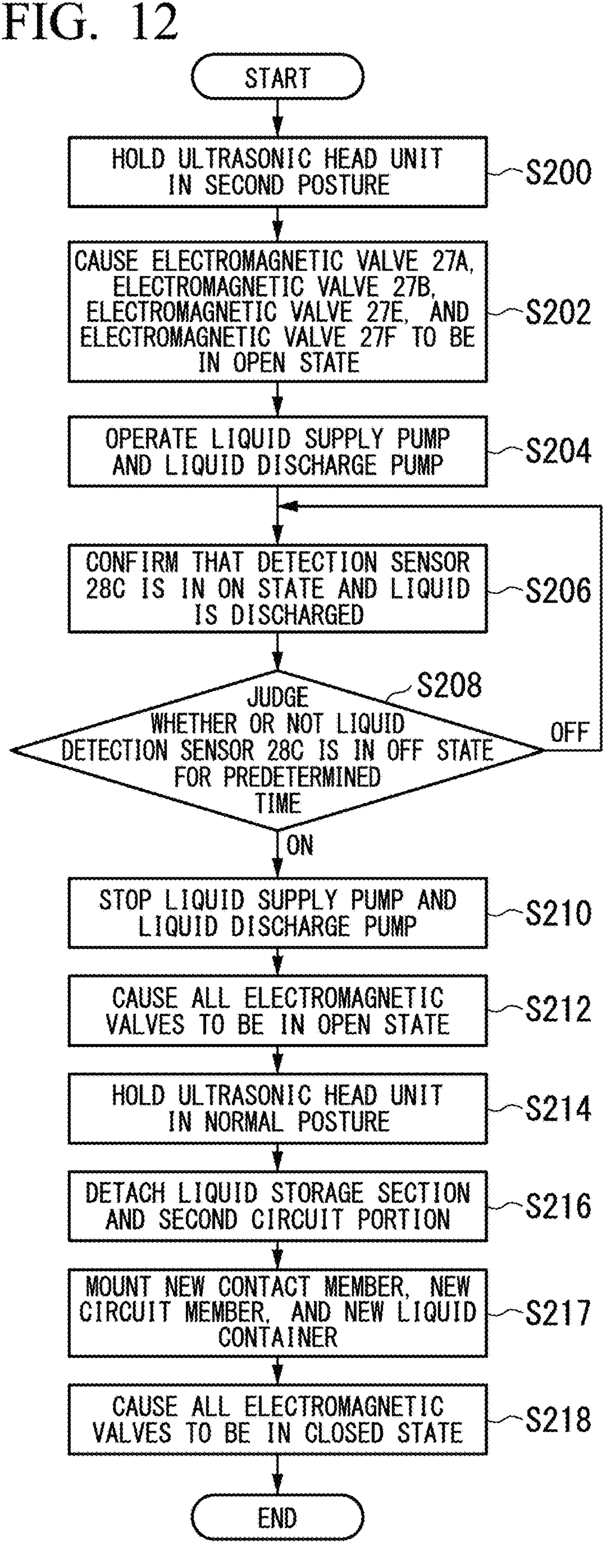
FIG. 12 is a flowchart showing a flow of processing executed in a liquid discharging step at the time of preparation for therapy.

FIG. 12 shows a flowchart of a flow of processing executed in the liquid discharging step at the time of preparation for therapy. The worker inputs an operation of starting detachment of the flow path members Rm of the fluid circuit section 25 through the input portion 49 of the control device 40. The control section 42 controls the robot arm 2 to move the ultrasonic head unit 10 to a position suitable for replacement work based on an input command signal for starting replacement. The control section 42 controls the robot arm 2 to hold the ultrasonic head unit 10 in the second posture (Step S200). The control section 42 causes the electromagnetic valve 27A provided on the upstream side of the liquid storage section 12, the electromagnetic valve 27B provided on the downstream side of the liquid storage section 12, the electromagnetic valve 27E provided in the flow path member R4 for liquid discharge, and the electromagnetic valve 27F provided on the flow path member R5 for atmospheric release to be in the open state (Step S202).

The control section 42 operates the liquid supply pump 26A and the liquid discharge pump 26B (Step S204). The control section 42 confirms that the liquid detection sensor

28C provided on the flow path member R4 for liquid discharge is in the ON state and a liquid is discharged from the flow path member R4 (Step S206). The control section 42 judges whether or not the liquid detection sensor 28C provided on the flow path member R4 for liquid discharge is in the OFF state for a predetermined time such as several seconds, for example (Step S208). When the liquid detection sensor 28C is in the OFF state in Step S208, the processing returns to Step S206. When it is in the ON state in Step S208, the control section 42 stops the liquid supply pump 26A and the liquid discharge pump 26B (Step S210). The control section 42 causes all the electromagnetic valves 27A to 27F to be in the open state (Step S212).

The control section 42 controls the robot arm 2 to hold the ultrasonic head unit 10 in a normal posture (Step S214). The control section 42 causes the display portion 48 to display an image for prompting replacement of the flow path members Rm of the fluid circuit section 25, the contact member 14, and the liquid container 29. The display portion 48 displays an image informing that detachment has ended. The worker detaches the flow path members Rm of the fluid circuit section 25 and the liquid container 29 together with the contact member 14 and the second attachment portion 21B (Step S216). The worker mounts new flow path members Rm of the fluid circuit section 25 and a new liquid container 29 together with a new contact member 14 and a new second attachment portion 21B, thereby completing replacement (Step S217). The worker performs an input operation indicating that detachment or replacement has ended using the input portion 49. The control section 42 causes all the electromagnetic valves 27A to 27F to be in the closed state based on an input operation (Step S218). Each of the foregoing steps is automatically performed by the control section 42, but it may be suitably stopped or started based on an operation input from the input portion 49 in the middle of the steps.

Figure 13:
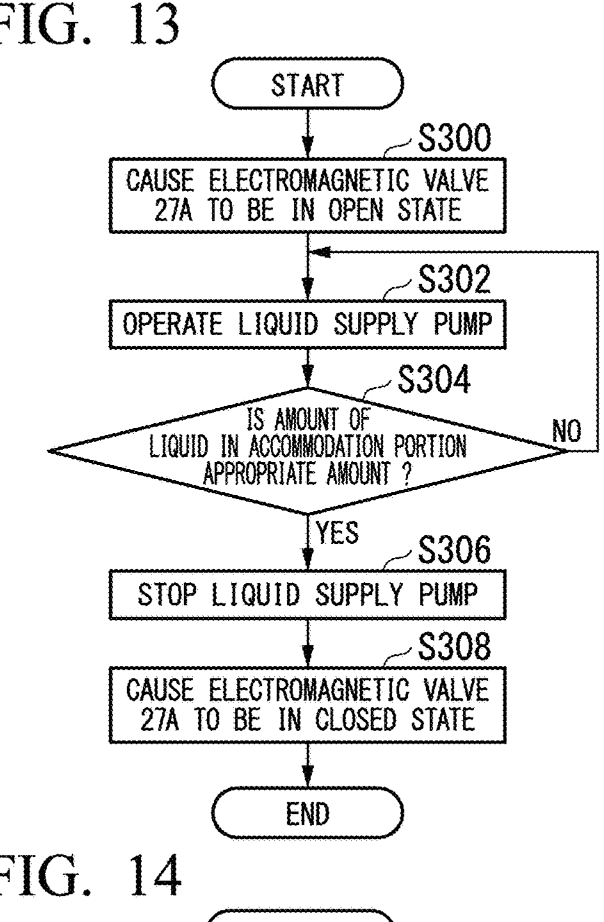
FIG. 13 is a flowchart showing a flow of processing executed when the amount of liquid inside a liquid storage section is increased.

FIG. 13 shows a flowchart of operation of processing executed when the amount of liquid inside the liquid storage section 12 is increased after the contact member 14, the liquid container 29, and the flow path members Rm of the fluid circuit section 25 are set and the inside thereof is filled with a medium liquid. The worker inputs an operation of increasing the amount of medium liquid flowing into the liquid storage section 12 using the input portion 49. The control section 42 causes the electromagnetic valve 27A provided on the upstream side of the liquid storage section 12 to be in the open state (Step S300). The control section 42 operates the liquid supply pump 26A based on an operation input using the input portion 49 (Step S302).

The worker looks at the amount of liquid in the liquid storage section 12 and judges whether or not the amount of liquid is an appropriate amount (Step S304). When it is judged that the amount of liquid is an appropriate amount, the worker performs an operation of inputting information indicating that the amount of liquid is an appropriate amount using the input portion 49. The control section 42 stops the liquid supply pump 26A based on an operation input through the input portion 49 (Step S306). The control section 42 causes the electromagnetic valve 27A provided on the upstream side of the liquid storage section 12 to be in the closed state (Step S308). The amount of liquid in the liquid storage section 12 can be increased based on the foregoing steps.

Figure 14:
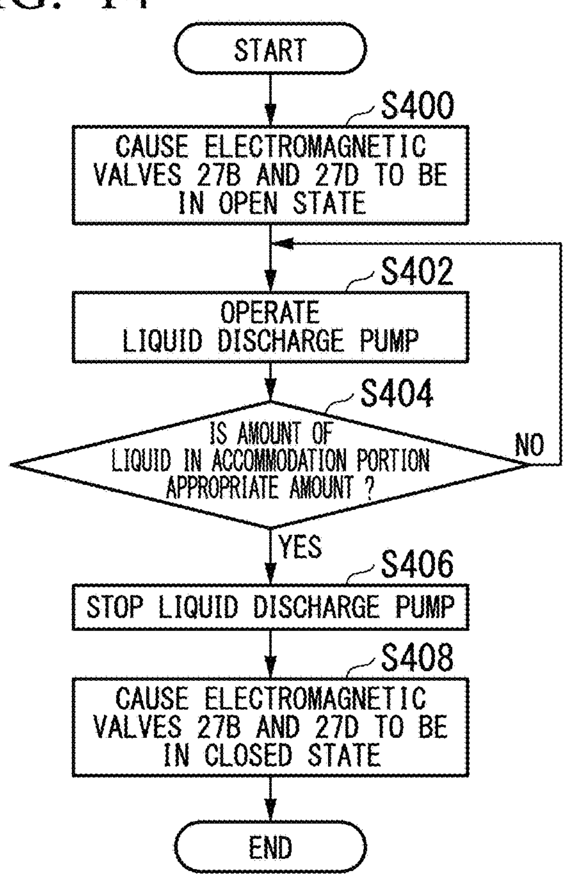
FIG. 14 is a flowchart showing a flow of processing executed when the amount of liquid inside the liquid storage section is reduced.

FIG. 14 shows a flowchart of operation of processing executed when the amount of liquid inside the liquid storage section 12 is reduced after the contact member 14, the liquid container 29, and the flow path members Rm of the fluid circuit section 25 are set, and the inside thereof is filled with a medium liquid. The worker inputs an operation of reducing the amount of medium liquid flowing into the liquid storage section 12 using the input portion 49. The control section 42 causes the electromagnetic valve 27B provided on the downstream side of the liquid storage section 12 and the electromagnetic valve 27D provided on the downstream side of the flow path member R2 to be in the open state (Step S400). The control section 42 operates the liquid discharge pump 26B based on an operation input using the input portion 49 (Step S402). The worker looks at the amount of liquid in the liquid storage section 12 and judges whether or not the amount of liquid is an appropriate amount (Step S404).

When it is judged that the amount of liquid is an appropriate amount, the worker performs an operation of inputting information indicating that the amount of liquid is an appropriate amount using the input portion 49. The amount of liquid may be automatically detected using a sensor or the like. The control section 42 stops the liquid discharge pump 26B based on an operation input using the input portion 49 (Step S406). The control section 42 causes the electromagnetic valve 27B provided on the downstream side of the liquid storage section 12 and the electromagnetic valve 27D provided on the downstream side of the flow path member R2 to be in the closed state (Step S408). The amount of liquid in the liquid storage section 12 can be reduced based on each of the foregoing steps.

The replacement target components such as the fluid circuit section 25 described above may be constituted as a unit based on the distribution form thereof. For example, the instrument attachment section 21, the fluid circuit section 25, and the liquid feeding control unit 42D may be constituted as a fluid operation device. The instrument attachment section 21 may be attached to a target other than the casing 20. That is, the fluid circuit section 25 that is a constituent element of the fluid operation device includes the plurality of flow path members Rm that are connected to the ultrasonic head unit 10 including the wave source 11A which radiates ultrasonic waves in a manner of focusing at a predetermined position inside a therapy object and the liquid storage section 12 which includes the contact portion 14A whose lower surface side comes into contact with the therapy object and is formed to have an adjustable volume, and through which a medium liquid filling the liquid storage section 12 and transmitting ultrasonic waves circulates.

The contact member 14 and the liquid container 29 can be integrated by being connected to each other via the flow path members Rm forming the liquid flow paths of the fluid circuit section 25 and the connection member. The contact member 14, the liquid container 29, and the flow path members Rm which have been integrated can be collectively detached for each patient or for each therapy every time therapy is performed, and they can be replaced with a new contact member 14, a new liquid container 29, and new flow path members Rm. In addition, replacement with a new contact member 14 and a new liquid container 29 can also be easily performed through preparation in which they are connected in advance to new flow path members Rm forming the liquid flow paths of the fluid circuit section 25 to be in an integrated state. The contact member 14 and the liquid container 29 have an integrated structure by being connected to the flow path members Rm via the connection member 14P. However, the contact member 14 and the liquid container 29 may be directly connected to the flow path members Rm to form an integrated structure without having the connection member 14P therebetween.

The fluid circuit section 25 includes the first circuit portion 25A which causes a medium liquid to circulate through the plurality of flow path members Rm, and the second circuit portion 25B which causes gas to flow into the first circuit portion 25A. The first circuit portion 25A includes the inflow circuit portion 25A1 which causes a medium liquid to flow into the liquid storage section 12, the outflow circuit portion 25A2 which causes a medium liquid to flow out from the liquid storage section 12, and the discharge circuit portion 25A3 which discharges a medium liquid to the outside.

The fluid circuit section 25 includes the circuit control instrument section 21S which is controlled for a flow of a medium liquid circulating through the plurality of flow path members Rm, and the instrument attachment section 21 on which the circuit control instrument section 21S is attached at a predetermined position. On the instrument attachment section 21, the circuit control instrument section 21S is attached to one surface side of the instrument attachment section 21, and the plurality of flow path members Rm are provided in an attachable/detachable manner with respect to the control instruments in the circuit control instrument section 21S.

The instrument attachment section 21 includes the first attachment portion 21A to which the control instruments in the circuit control instrument section 21S are attached, and the second attachment portion 21B which is provided in an attachable/detachable manner with respect to the first attachment portion 21A. The first attachment portion 21A includes the detachable engagement portions 21K which cause the second attachment portion 21B to be engaged and positionally set at a predetermined position. The second attachment portion 21B includes the detachable attachment member 21P to which the plurality of flow path members Rm are attached. In the detachable attachment member 21P, the mounting engagement portions 21Q which engage with the detachable engagement portions 21K are formed. In the detachable attachment member 21P, the plurality of flow path members Rm are positionally set and attached at a plurality of predetermined positions by the plurality of flow path support portions 21M. At the plurality of predetermined positions, the cutout portions 21Ro are formed as necessary at positions corresponding to the positions of the control instruments in the circuit control instrument section 21S. The flow path members Rm are disposed so as to be exposed through the cutout portions 21Ro.

The liquid feeding control unit 42D that is a constituent element of the fluid operation device controls the fluid circuit section 25 to adjust the storage amount of a medium liquid stored in the liquid storage section 12, discharge a medium liquid from the fluid circuit section 25, and supply a new medium liquid to the fluid circuit section 25. The liquid feeding control unit 42D may perform individual authentication of the fluid circuit section 25 between the fluid circuit section 25 and the control device 40 and may perform communication for diagnosing operation of the circuit control instrument section 21S. The liquid feeding control unit 42D may be provided on the control device 40 side.

Figure 15:
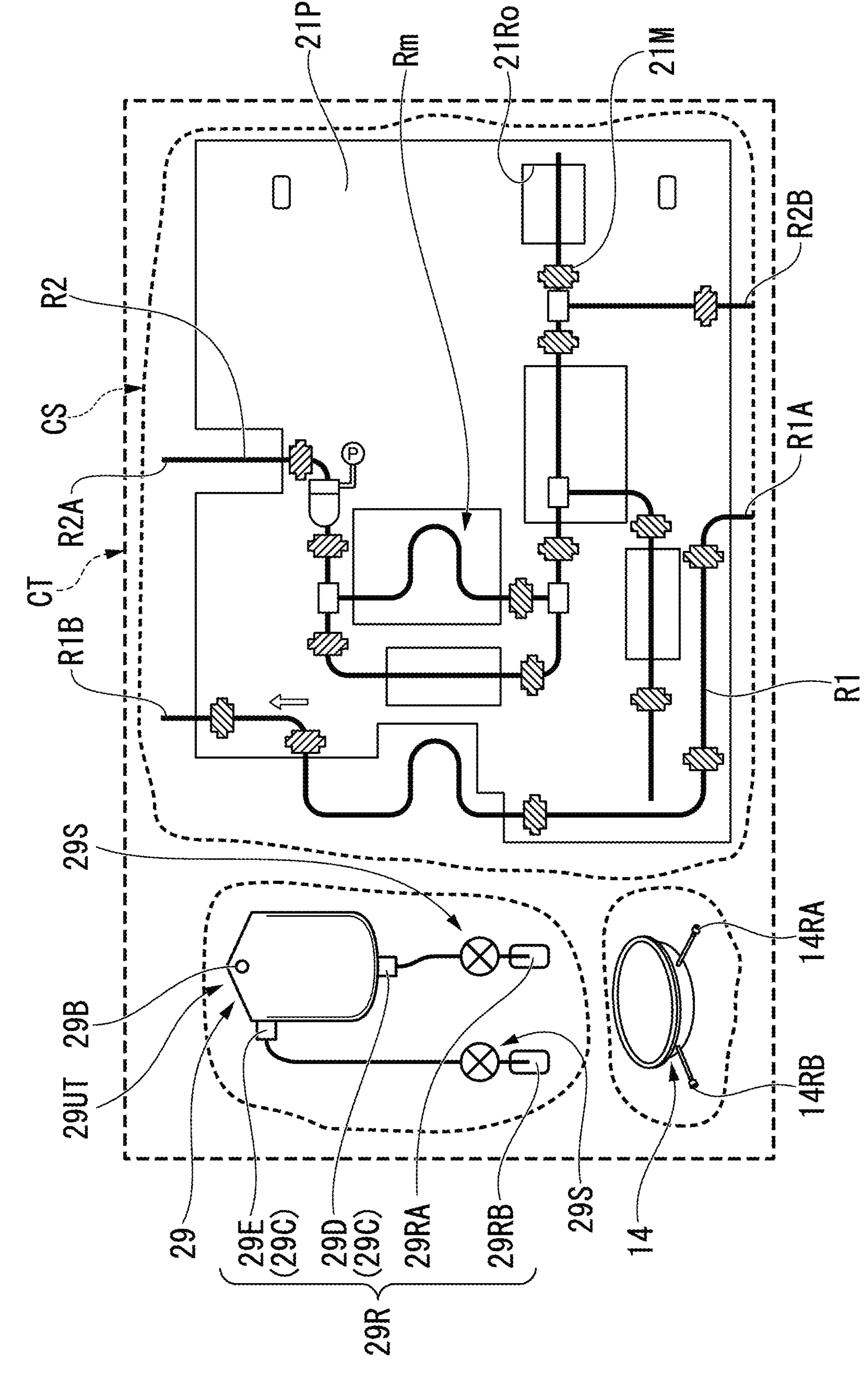
FIG. 15 is a view schematically showing a fluid circuit set in which a replacement target is accommodated and packaged in an accommodation body.

In addition, in the constituents of the fluid circuit section 25 described above, a fluid circuit set with a packaged replacement target may be constituted. FIG. 15 shows a fluid circuit set CS with a packaged replacement target. In the fluid circuit set CS, the plurality of flow path members Rm are mounted in the detachable attachment member 21P in advance at positions corresponding to the circuit control instrument section 21S provided in the first attachment portion 21A and are accommodated in an accommodation body CT in a state of constituting part of the circuit of the fluid circuit section 25. The fluid circuit set CS includes the plurality of flow path members Rm for circulating a medium liquid filling the liquid storage section 12 and transmitting ultrasonic waves. The plurality of flow path members Rm is connected to the ultrasonic head unit 10 that includes the wave source 11A which radiates ultrasonic waves in a manner of focusing at a predetermined position inside a therapy object, and the liquid storage section 12 which includes the contact portion 14A whose lower surface side comes into contact with a therapy object and is formed to have an adjustable volume.

The fluid circuit set CS includes the detachable attachment member 21P to which the plurality of flow path members Rm are attached. On the detachable attachment member 21P, the plurality of flow path members Rm are positionally set and attached at a plurality of predetermined positions by the plurality of flow path support portions 21M. At the plurality of predetermined positions, the cutout portions 21Ro are formed as necessary at positions corresponding to the positions of the control instruments in the circuit control instrument section 21S. In the present Example, since the cutout portions 21Ro corresponding to the plurality of control instruments are necessary, the plurality of cutout portions 21Ro are formed. The plurality of flow path members Rm are disposed so as to be exposed through the plurality of cutout portions 21Ro.

In addition, the fluid circuit set CS is accommodated in the accommodation body CT which can accommodate the detachable attachment member 21P in a state in which the plurality of flow path members Rm are attached. The accommodation body CT may also accommodate the contact member 14. For example, the accommodation body CT is constituted of a box body and a packaging member. The box body is a container which is formed of a material such as recyclable paper used during a circulation process. The packaging member is a cushioning material filling a gap between an accommodation target accommodated in the box body and the inner wall of the box body. The packaging member may be a member in which an internal space having a shape of an accommodation target is formed, or many cushioning materials formed to have the shape of the accommodation target may fill a gap between an accommodation target and the box body. In addition, the fluid circuit set CS may be accommodated in a bag-shaped package body and then may be accommodated in the accommodation body CT.

In addition, the fluid circuit set CS may include the contact member 14 which is attached to the ultrasonic head unit 10. The contact member 14 is formed to include the contact portion 14A which is provided in the lower portion of the contact member 14, and the mounting portion 14B which is formed to extend in a manner of surrounding an upper part around the contact portion 14A and mounted on the mounting target part of the ultrasonic head unit 10. The mounting portion 14B includes the inflow connection portion 14RA which is provided at the first position connected to the inflow circuit portion 25A1 of the fluid circuit section 25 causing a medium liquid to flow into the liquid storage section 12, and the outflow connection portion 14RB which is provided at the second position different from the first position in a plan view and connected to the outflow circuit portion 25A2 of the fluid circuit section 25 causing a medium liquid to flow out from the liquid storage section 12. In addition, the contact member 14 may be accommodated in a bag-shaped package body and then may be accommodated in the accommodation body CT.

In addition, the fluid circuit set CS may include the medium liquid unit 29UT which includes a medium liquid. The medium liquid unit 29UT may include the liquid container 29 which accommodates a medium liquid, and a connection portion 29R which connects the liquid container 29 and the fluid circuit section 25. The liquid container 29 has an accommodation space which accommodates a medium liquid. The connection portion 29R is connected to the fluid circuit section 25 which includes the plurality of flow path members Rm for circulating a medium liquid. The liquid container 29 is provided with the engagement portion 29B which engages with the support portion 23. The connection portion 29R includes the first connection portion 29D which is connected to the liquid container 29, and the second connection portion 29E which is connected to the liquid container 29. In addition, the connection portion 29R includes an inflow connection portion 29RA to which the inflow circuit portion 25A1 is connected, and an outflow connection portion 29RB which is connected to the outflow circuit portion 25A2. Since the liquid container 29 is prepared in a state of accommodating an unused medium liquid, the liquid container 29 includes outflow restriction members 29S which prevent a medium liquid from flowing out from the liquid container 29. The outflow restriction members 29S are provided respectively between the liquid container 29 and the inflow connection portion 29RA and between the liquid container 29 and the outflow connection portion 29RB, and a Klemme, which is used as a general medical care member, is employed as the outflow restriction members 29S for restriction and the adjustment of the flow rate. The inflow connection portion 29RA and the outflow connection portion 29RB are connection members, and Luer lock connectors are used as the connection members as general medical care members. The medium liquid accommodated in the liquid container 29 is degassed water from which dissolved gas has been removed. The liquid container 29 may be accommodated in the accommodation body CT. In addition, the liquid container 29 may be accommodated in a bag-shaped package body and then may be accommodated in the accommodation body CT.

In addition, the fluid circuit set CS described above may be accommodated in the accommodation body CT in an integrated state in which the contact member 14 and the liquid container 29 are connected in advance to the plurality of flow path members Rm mounted on the detachable attachment member 21P.

As described above, the ultrasonic therapy device 1 can maintain the performance of a medium liquid for each therapy by replacing the flow path members Rm of the fluid circuit section 25, the contact member 14, and the liquid container 29 with the new ones in which a new medium liquid (degassed water) is included in the liquid container 29 for each therapy of the patient K. According to the ultrasonic therapy device 1, since the flow path members Rm of the fluid circuit section 25, the contact member 14, and the liquid container 29 are constituted such that the replacement work thereof is simple work such as only connection, attachment, and detachment of the plurality of flow path members Rm, a workload can be reduced. According to the ultrasonic therapy device 1, since the plurality of flow path members Rm of the fluid circuit section 25 are unitized in a state in which part of the flow paths in the fluid circuit section 25 are formed in advance, the plurality of flow path members Rm can be reliably attached at a position corresponding to the position of the circuit control instrument section 21S provided in the instrument attachment section 21. According to the ultrasonic therapy device 1, since the plurality of flow path members Rm in which a medium liquid circulates and stays, the contact member 14, and the liquid container 29 are replaced with the new ones in which a new medium liquid (degassed water) is included in the liquid container for each therapy, appropriate hygiene management can be performed.

The constituent elements, which include the main control unit 42A, the robot arm control unit 42B, the ultrasonic control unit 42C, and the liquid feeding control unit 42D, constituting the control section 42 described above are realized by a hardware processor such as a central processing unit (CPU) executing a program (software), for example. Some or all of these constituent elements may be realized by hardware (circuit portion; including circuitry) such as a large-scale integration (LSI), an application specific integrated circuit (ASIC), a field-programmable gate array (FPGA), or a graphics processing unit (GPU), or may be realized by software and hardware in cooperation. A program may be stored in a storage device (a storage device including a non-transitory storage medium) in advance such as a hard disk drive (HDD) or a flash memory, or may be stored in an attachable/detachable storage medium (a non-transitory storage medium) such as a DVD or a CD-ROM such that the program is installed in the storage device when the storage medium is mounted in a drive device. In the processing executed by the foregoing control section 42, processing may be performed by a computer on a server using cloud computing. In the processing executed by the foregoing control section 42, the functions may be executed by a plurality of distributed computers in a distributed manner.

In the fluid circuit section 25 described above, the second circuit portion 25B which causes gas to flow into the first circuit portion 25A is provided to be connected to the outflow circuit portion 25A2 provided for circulating a liquid from the liquid storage section 12 (in FIG. 3, the contact member 14) to the liquid container 29. However, the second circuit portion 25B may be provided to be connected to the inflow circuit portion 25A1 provided for circulating a liquid from the liquid container 29 to the liquid storage section 12.

Figure 16:
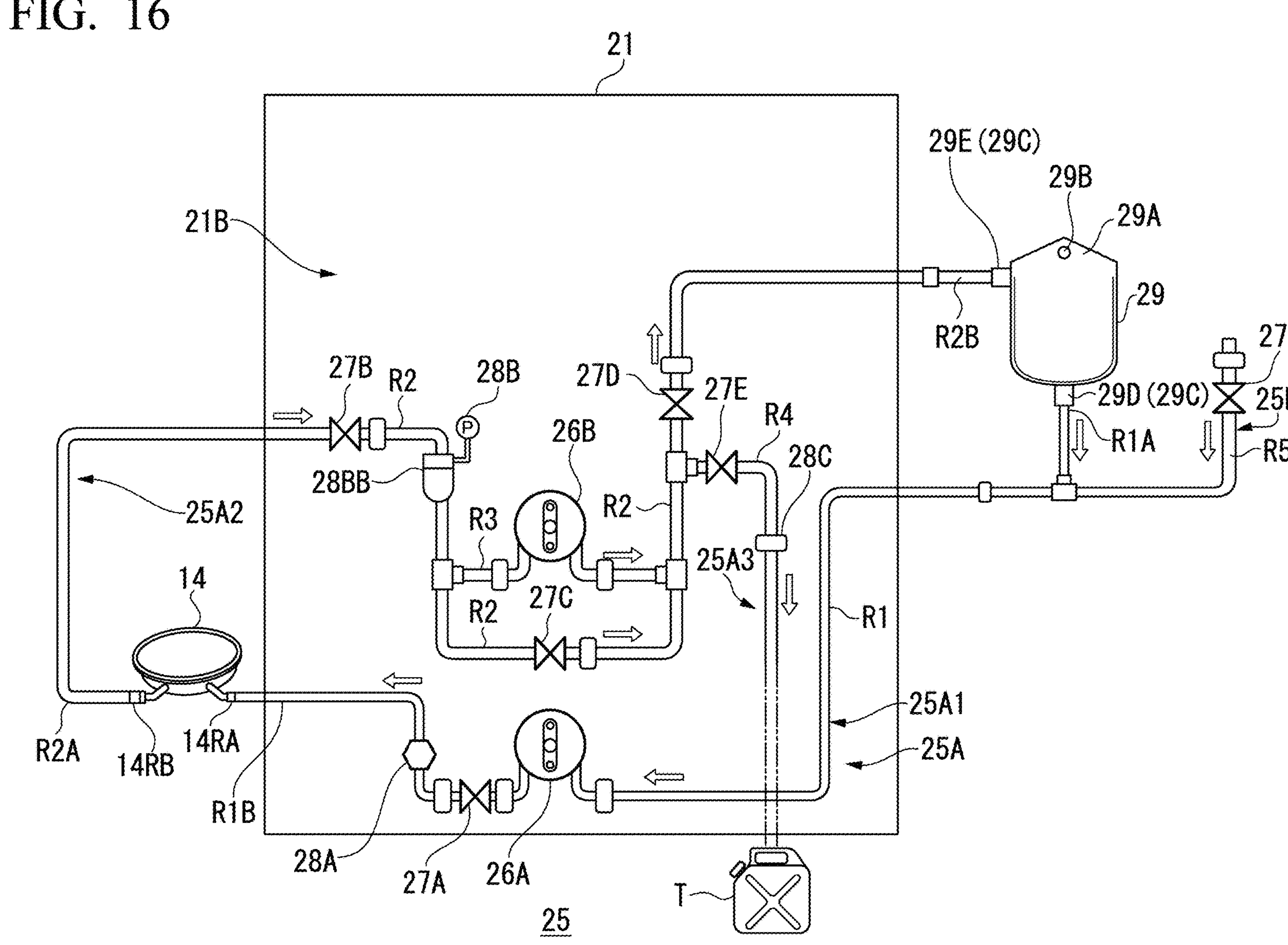
FIG. 16 is a view showing another constitution of the fluid circuit section.

As shown in FIG. 16, in the fluid circuit section 25, the second circuit portion 25B which causes gas to flow into the first circuit portion 25A is provided by connecting the flow path member R5 of the second circuit portion 25B to a part in the middle of the flow path member R1 of the inflow circuit portion 25A1 provided for circulating a liquid from the liquid container 29 to the liquid storage section 12 (in FIG. 16, the contact member 14). Specifically, the second circuit portion 25B is provided by connecting the flow path member R5 to a part in the middle of the flow path member R1 between the liquid container 29 and the liquid supply pump 26A, that is, a part in the middle of the flow path member R1 on the side of the first connection portion 29D of the liquid container 29. By connecting the second circuit portion 25B to a part in the middle of the flow path member R1 of the first circuit portion 25A between the liquid container 29 and the liquid supply pump 26A, and opening the inside of the flow path members Rm forming the flow paths of the liquid container 29, the liquid storage section 12, and the fluid circuit section 25 to the atmosphere, the inside is prevented from becoming a negative pressure due to outflow of a liquid so that the liquid can be smoothly discharged from the inside. The second circuit portion 25B which causes gas to flow in may be provided to be connected to the outflow circuit portion 25A2 provided for circulating a liquid to the liquid container 29 as shown in FIG. 3, and two second circuit portions 25B may be provided by further adding the second circuit portion 25B connected to the inflow circuit portion 25A1 for circulating a liquid from the liquid container 29 to the liquid storage section 12 as shown in FIG. 16.

Modification Example 1

A modification example of the casing 20 according to the present invention is described below.

Figure 17:
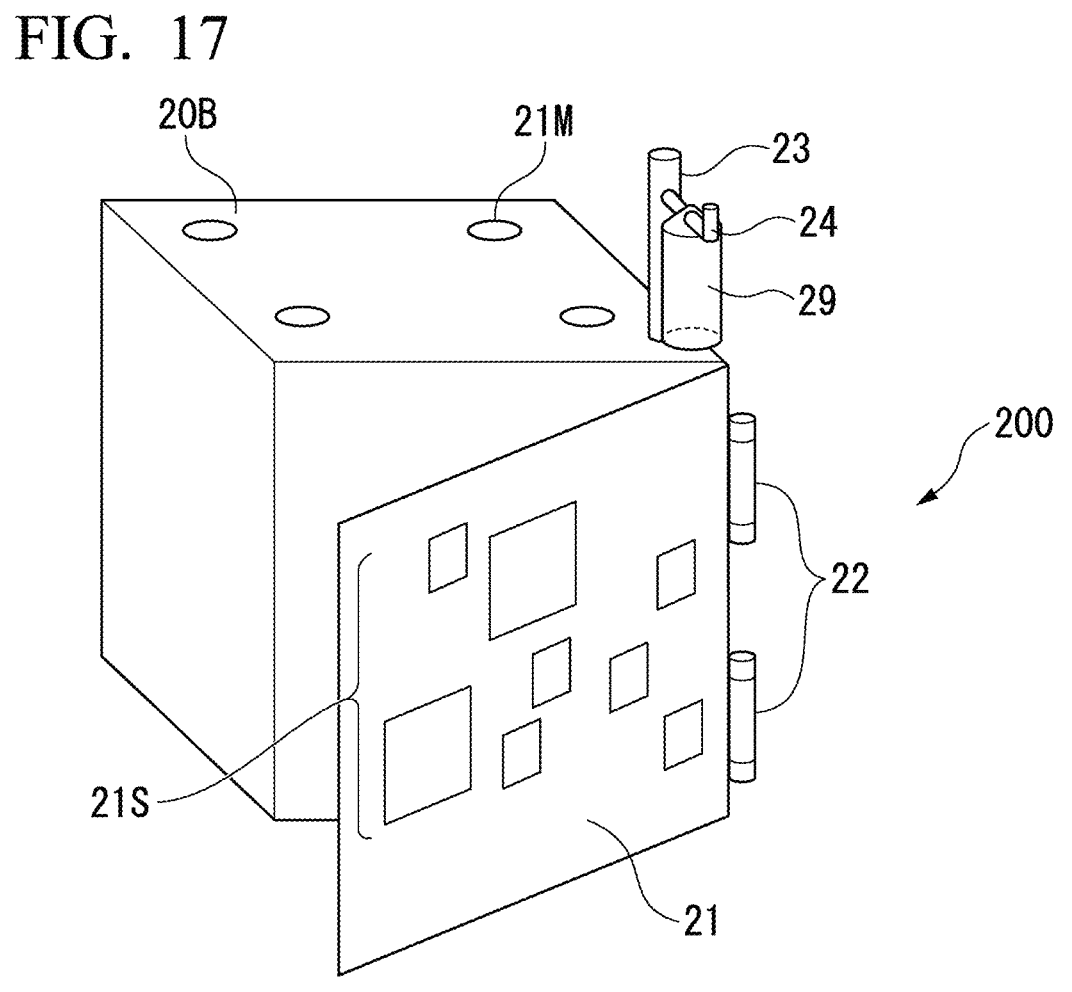

As shown in FIG. 17, a plurality of flow path support portions 21M are disposed on an upper surface of a casing main body 20B of a casing 200 in the present modification example. That is, the casing 200 in the present modification example further includes the plurality of flow path support portions 21M together with the support portion 23 on the upper surface thereof.

The flow path support portions 21M disposed on the upper surface of this casing main body 20B are constituted such that the plurality of flow path members Rm can be attached thereto. Accordingly, the plurality of flow path members Rm are positionally set and attached at a plurality of predetermined positions on the upper surface of the casing main body 20B by the plurality of flow path support portions 21M.

Figure 18:
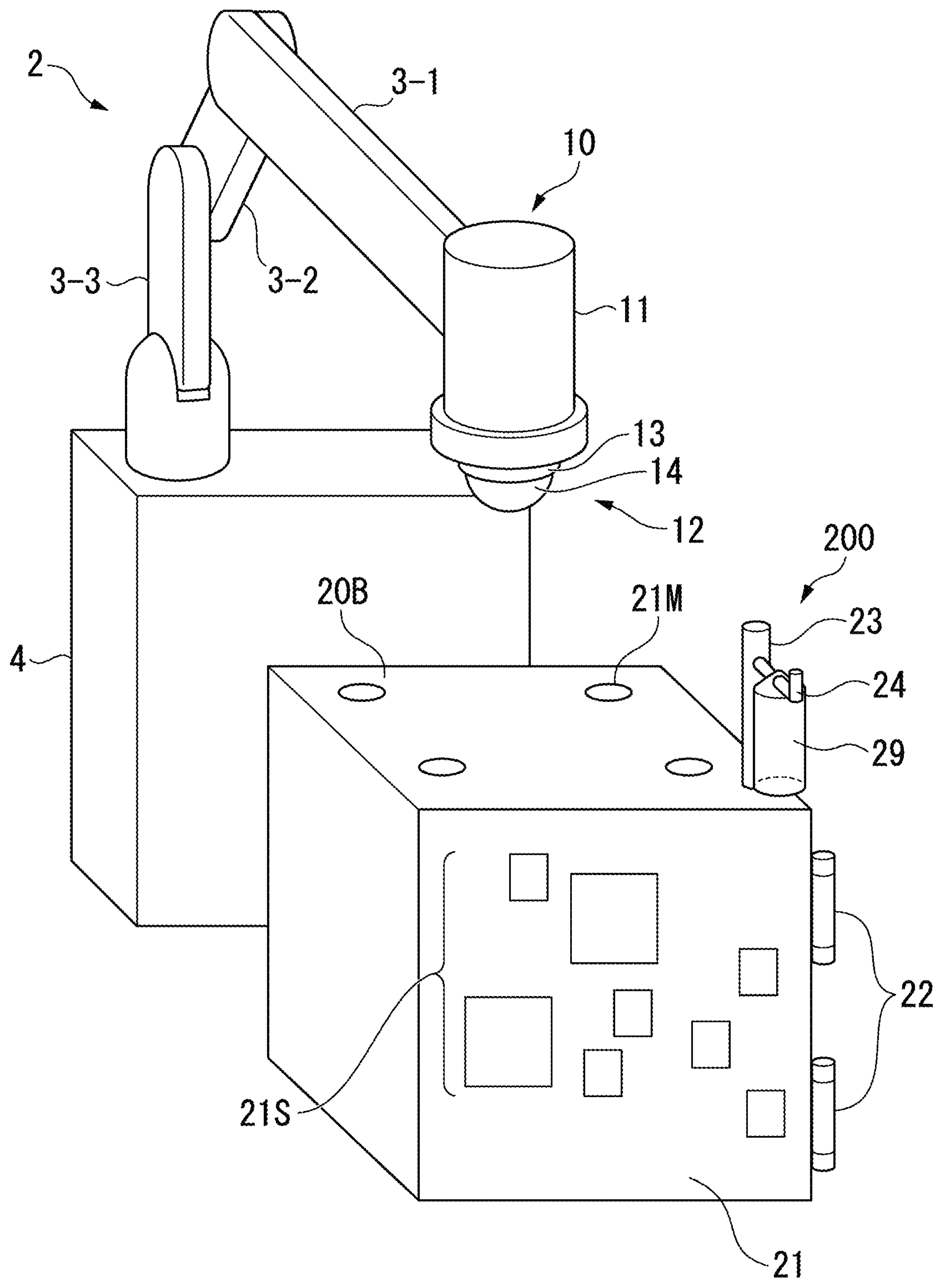
FIG. 18 is another perspective view showing the casing according to Modification Example 1 of the present invention.

FIG. 18 shows the casing 200 and the ultrasonic head unit 10 in the present modification example.

In the liquid supplying step at the time of preparation for therapy and the liquid discharging step at the time of preparation for therapy, the ultrasonic head unit 10 moves to a predetermined position (water supply position) shown in FIG. 18. In addition, when the contact member 14 (liquid storage section 12), the liquid container 29, and the flow path members Rm are replaced, the ultrasonic head unit 10 moves to a predetermined position shown in FIG. 18.

The predetermined position of the ultrasonic head unit 10 shown in FIG. 18 is a position where the ultrasonic head unit 10 is positioned at least above the upper surface of the casing 200 (casing main body 20B).

The predetermined position of the ultrasonic head unit 10 shown in FIG. 18 is preferably a position where the ultrasonic head unit 10 is positioned above a region surrounded by the plurality of flow path support portions 21M disposed on the upper surface of the casing main body 20B and overlaps the region in a view in the up-down direction.

That is, a projection region on the upper surface of the casing 200 (casing main body 20B) which coincides with the predetermined position (the water supply position) of the ultrasonic head unit 10 in a view in the up-down direction is surrounded by the plurality of flow path support portions 21M which are disposed on the upper surface of the casing 200 (casing main body 20B).

Due to such a constitution, in the present modification example, during the liquid supplying step at the time of preparation for therapy and the liquid discharging step at the time of preparation for therapy, and when the contact member 14 (liquid storage section 12), the liquid container 29, and the flow path members Rm are replaced, work can be performed by moving the ultrasonic head unit 10 to a position above the casing 200.

Accordingly, since liquid supply and liquid discharge with respect to the contact member 14 (liquid storage section 12) can be performed near other members provided on the casing main body 20B, the flow of traffic of a worker can be shortened, and liquid supply and liquid discharge can be performed more efficiently.

In addition, since the contact member 14 (liquid storage section 12), the liquid container 29, and the flow path members Rm can be replaced while the contact member 14 (liquid storage section 12), the liquid container 29, and the flow path members Rm are brought close to each other, replacement can be performed more efficiently.

Modification Example 2

A modification example of the instrument attachment section 21 according to the present invention is described below.

Figure 19:
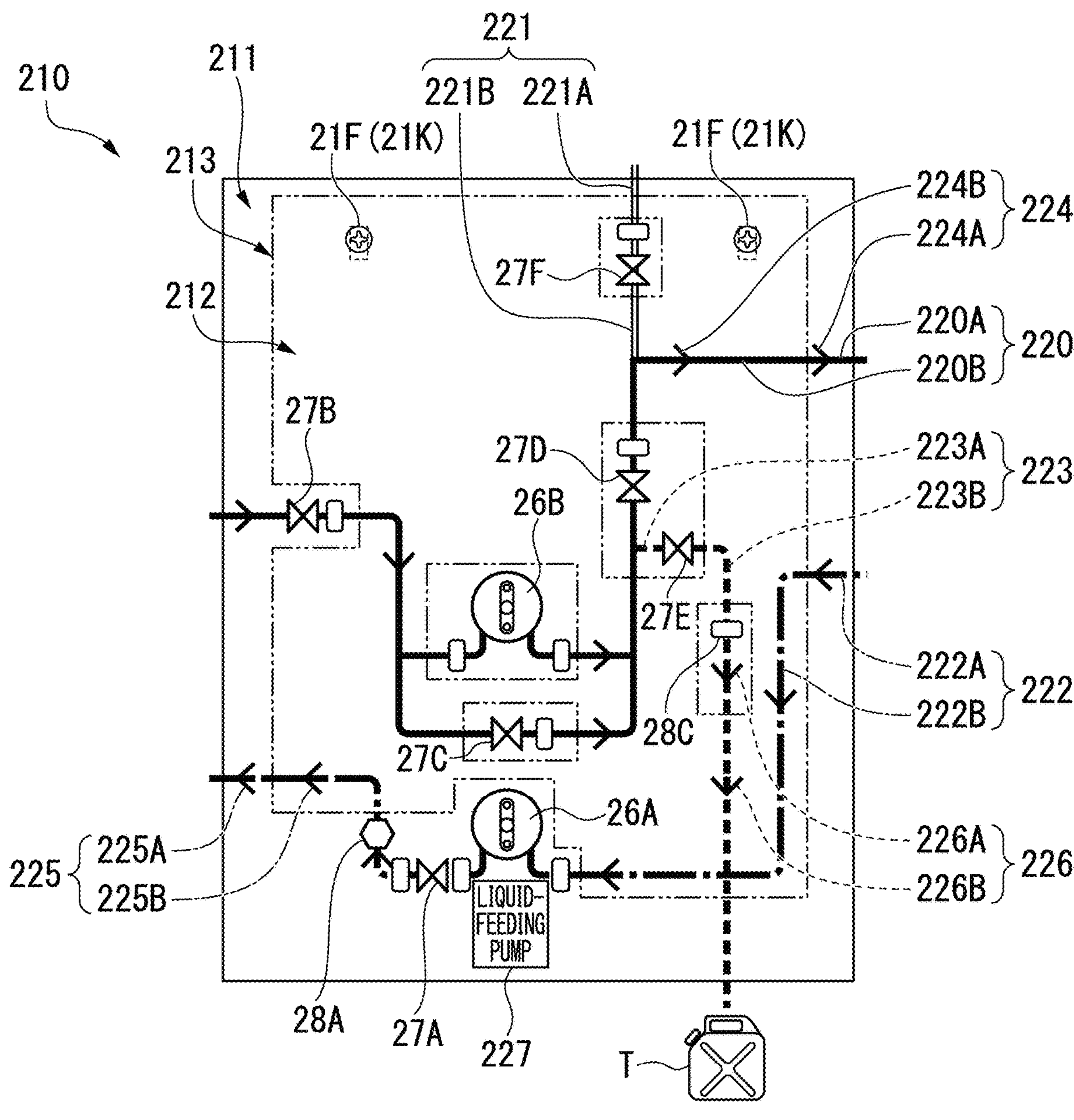
FIG. 19 is a view showing an instrument attachment section according to Modification Example 2 of the present invention.

As shown in FIG. 19, an instrument attachment section 210 according to the present modification example includes a plurality of identification portions 220 to 223 provided on a first attachment portion 211 and a second attachment portion 212 (detachable attachment member 213). The plurality of identification portions 220 to 223 further include arrow portions 224, 225, and 226, and an identification character portion 227.

The identification portions 220 to 223 are guide portions indicating predetermined positions where the flow path members Rm are disposed. The identification portions 220 to 223 are indicated in different colors (colored in different colors).

The identification portion 220 (outflow identification portion) is indicated by a solid line in FIG. 19, and it is indicated in blue, for example. The identification portion 220 indicates a predetermined position where the flow path members R2 and R3 are disposed. The identification portion 220 guides the outflow circuit portion 25A2. The identification portion 220 includes an identification portion 220A which is provided on the first attachment portion 211, and an identification portion 220B which is provided on the second attachment portion 212.

The identification portion 221 (second-circuit-portion identification portion) is indicated by an outlined line in FIG. 19, and it is indicated in yellow, for example. The identification portion 221 indicates a predetermined position where the flow path member R5 is disposed. The identification portion 221 guides the second circuit portion. The identification portion 221 includes an identification portion 221A which is provided on the first attachment portion 211, and an identification portion 221B which is provided on the second attachment portion 212.

The identification portion 222 (inflow identification portion) is indicated by a dotted dashed line in FIG. 19, and it is indicated in red, for example. The identification portion 222 indicates a predetermined position where the flow path member R1 is disposed. The identification portion 222 guides the inflow circuit portion 25A1. The identification portion 222 includes an identification portion 222A which is provided on the first attachment portion 211, and an identification portion 222B which is provided on the second attachment portion 212.

The identification portion 223 (discharge identification portion) is indicated by a dashed line in FIG. 19, and it is indicated in green, for example. The identification portion 223 indicates a predetermined position where the flow path member R4 is disposed. The identification portion 223 guides the discharge circuit portion 25A3. The identification portion 223 includes an identification portion 223A which is provided on the first attachment portion 211, and an identification portion 223B which is provided on the second attachment portion 212.

In addition, the identification portions 220, 222, and 223 respectively include the arrow portions 224, 225, and 226.

The arrow portions 224 to 226 are parts indicating the circulation direction of a medium liquid circulating through the flow path members Rm which are disposed on the identification portions 220, 222, and 223. The arrow portions 224 to 226 are indicated in different colors (colored in different colors).

The identification portion 220 includes the arrow portion 224. For example, the arrow portion 224 is indicated in blue. The arrow portion 224 includes an arrow portion 224A which is provided on the first attachment portion 211, and an arrow portion 224B which is provided on the second attachment portion 212.

The identification portion 222 includes the arrow portion 225. For example, the arrow portion 225 is indicated in red. The arrow portion 225 includes an arrow portion 225A which is provided on the first attachment portion 211, and an arrow portion 225B which is provided on the second attachment portion 212.

The identification portion 223 includes the arrow portion 226. For example, the arrow portion 226 is indicated in green. The arrow portion 226 includes an arrow portion 226A which is provided on the first attachment portion 211, and an arrow portion 226B which is provided on the second attachment portion 212.

The identification character portion 227 is provided on the first attachment portion 211. The identification character portion 227 indicates members (the pump portions 26, the valve portions 27, and the liquid detection portions 28) which are provided in the vicinity of the position where the identification character portion 227 is provided.

In the example in FIG. 19, the identification character portion 227 indicates that the liquid supply pump 26A is provided in the vicinity of the position where the identification character portion 227 is provided.

Due to such a constitution, in the present modification example, a worker can mount the flow path members Rm on the instrument attachment section 210 using the identification portions 220 to 223 as guidelines. In addition, by referring to the arrow portions 224 to 226, the worker can mount the flow path members Rm on the instrument attachment section 21 while exactly ascertaining the circulation direction of a medium liquid in the flow path members Rm. In addition, when an abnormality occurs in the instruments, the worker can easily identify the instrument in which an abnormality has occurred by referring to the identification character portion 227.

Therefore, the worker can perform work of mounting the flow path members Rm more efficiently and can prevent occurrence of an error in the mounting place. In addition, since an instrument in which an abnormality has occurred can be easily identified, maintainability of the instrument attachment section 210 can be improved.

In the constitution of the foregoing modification example, the flow path members Rm disposed on the identification portions 220 to 223 may be indicated in the same color as the identification portions where they are disposed (may be colored in different colors). That is, the flow path members disposed on the respective identification portions may be indicated in different colors (may be colored in different colors).

The flow path members R2 and R3 disposed on the identification portion 220 (outflow identification portion) may be indicated in blue, for example.

The flow path member R5 disposed on the identification portion 221 (second-circuit-portion identification portion) may be indicated in yellow, for example.

The flow path member R1 disposed on the identification portion 222 (inflow identification portion) may be indicated in red, for example.

The flow path member R4 disposed on the identification portion 223 (discharge identification portion) may be indicated in green, for example.

The worker does not necessarily need to dispose all the flow path members Rm exactly on the identification portions 220 to 223, and part of the flow path members Rm may be disposed in the vicinity of the identification portions 220 to 223.

Some or all of the identification portions 220 to 223 may not be classified by color.

The identification portions 220 to 223 are indicated by lines having different shapes. However, some or all of them may be indicated by lines having the same shape (for example, solid lines), or some or all of them may not be provided.

Some or all of the arrow portions 224 to 226 may not be classified by color, or some or all of them may not be provided.

The identification character portion 227 is not limited to the example shown in FIG. 19 and may indicate that a member other than the liquid supply pump 26A is provided in the vicinity of the position where the identification character portion 227 is provided. The identification character portion 227 may be provided on the second attachment portion 212. A plurality of identification character portions 227 may be provided, and the identification character portions 227 may indicate respective members provided in the vicinity of the positions where the identification character portions 227 is provided. The identification character portion 227 may not be provided.

Since the flow path member R5 for circulating air is disposed on the identification portion 221, the identification portion 221 includes no arrow portion, but it may include an arrow portion. In this case, the arrow portion of the identification portion 221 indicates a direction in which air circulates through the flow path member R5.

Modification Example 3

An upper surface 230 which is a modification example of the upper surface of the casing 20 (casing main body 20A) according to the present invention is described below.

Figure 20:
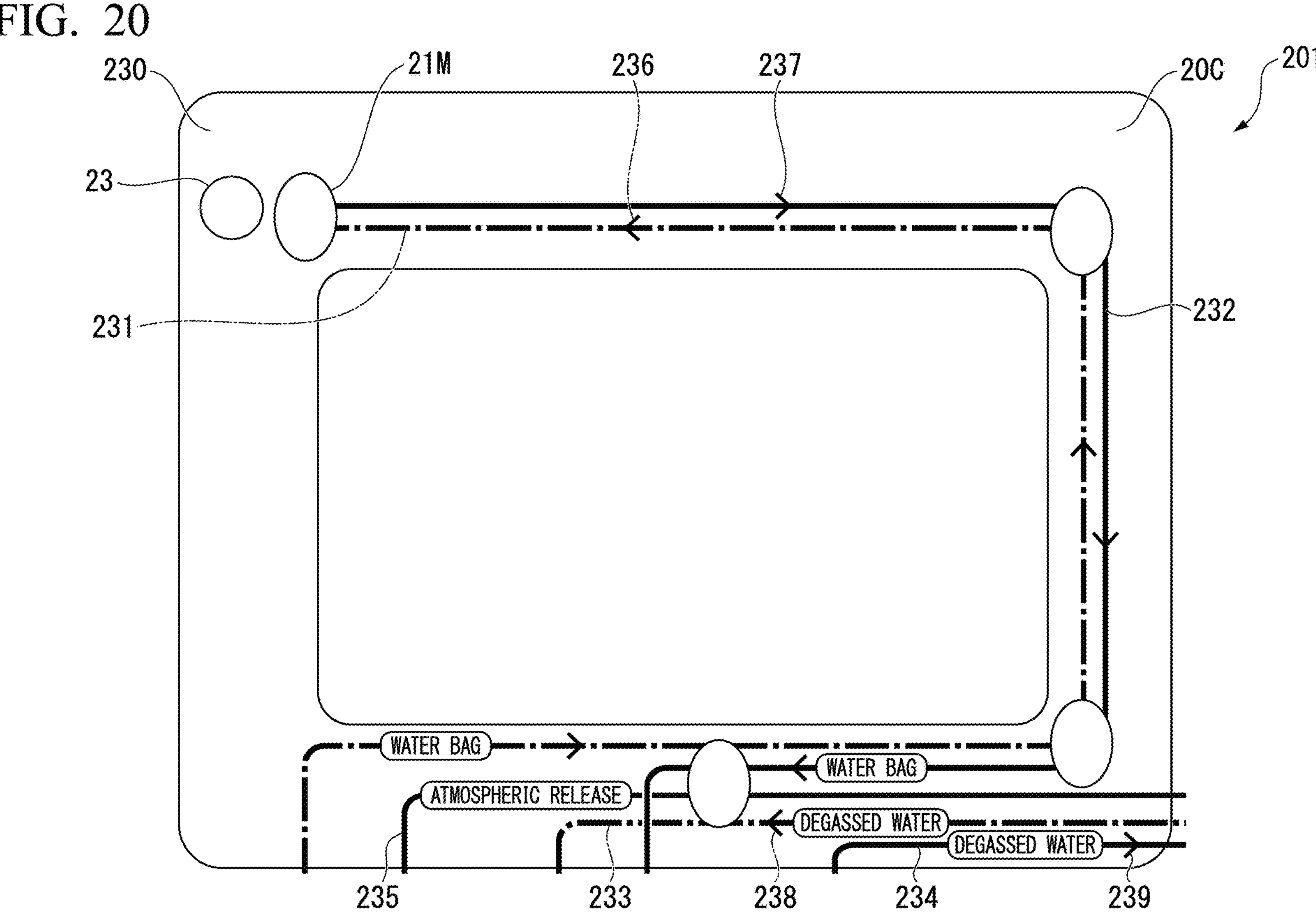
FIG. 20 is a view showing a casing according to Modification Example 3 of the present invention.

As shown in FIG. 20, the upper surface 230 of a casing 201 (casing main body 20C) according to the present modification example includes the support portion 23, a plurality of flow path support portions 21M, identification portions 231 to 235, and arrow portions 236 to 239.

The identification portions 231 to 235 are guide portions indicating predetermined positions where the flow path members Rm are disposed. The identification portions 231 and 233, the identification portions 232 and 234, and the identification portion 235 are indicated in different colors (colored in different colors).

In addition, the identification portions 231 to 235 each include a character portion. The character portion indicates a part to which the flow path members Rm disposed on the identification portions 231 to 235 are connected (connection destination, a target to be connected) or a substance which circulates through the flow path members Rm (circulating matter, a substance which circulates).

The identification portion 231 is indicated by a dotted dashed line in FIG. 20, and it is indicated in red, for example. The identification portion 231 indicates a predetermined position where the flow path member R1 is disposed. The character portion included in the identification portion 231 indicates that the flow path member R1 disposed on the identification portion 231 is connected to the liquid container 29.

The identification portion 232 is indicated by a solid line in FIG. 20, and it is indicated in blue, for example. The identification portion 232 indicates a predetermined position where the flow path member R2 is disposed. The character portion included in the identification portion 232 indicates that the flow path member R2 disposed on the identification portion 232 is connected to the liquid container 29.

The identification portion 233 is indicated by a dotted dashed line in FIG. 20, and it is indicated in red, for example. The identification portion 233 indicates a predetermined position where the flow path member R1 is disposed. The character portion included in the identification portion 233 indicates that degassed water circulates through the flow path member R1 disposed on the identification portion 233.

The identification portion 234 is indicated by a solid line in in FIG. 20, and it is indicated in blue, for example. The identification portion 234 indicates a predetermined position where the flow path member R2 is disposed. The character portion included in the identification portion 234 indicates that degassed water circulates through the flow path member R2 disposed on the identification portion 234.

The identification portion 235 is indicated by an outlined line in FIG. 20, and it is indicated in yellow, for example. The identification portion 235 indicates a predetermined position where the flow path member R5 is disposed. The character portion included in the identification portion 235 indicates that air (atmospheric air) circulates through the flow path member R5 disposed on the identification portion 235.

In addition, the identification portions 231 to 234 respectively include the arrow portions 236 to 239. The arrow portions 236 to 239 are parts indicating the circulation direction of a medium liquid circulating through the flow path members Rm disposed on the identification portions 231 to 234. The arrow portions 236 to 239 are indicated in different colors (colored in different colors).

The identification portion 231 includes the arrow portion 236. The arrow portion 236 is indicated in red, for example.

The identification portion 232 includes the arrow portion 237. The arrow portion 237 is indicated in blue, for example.

The identification portion 233 includes the arrow portion 238. The arrow portion 238 is indicated in red, for example.

The identification portion 234 includes the arrow portion 239. The arrow portion 239 is indicated in blue, for example.

Due to such a constitution, in the present modification example, a worker can mount the flow path members Rm on the upper surface 230 of the casing 201 (casing main body 20C) using the identification portions 231 to 234 as guidelines. In addition, the worker can mount the flow path members Rm on the upper surface 230 while exactly ascertaining the circulation direction of a medium liquid in the flow path members Rm. In addition, the worker can mount the flow path members Rm on the upper surface 230 while exactly ascertaining a part to which the flow path members Rm are connected or a substance which circulates through the flow path members Rm.

Therefore, the worker can perform work of mounting the flow path members Rm more efficiently and can prevent occurrence of an error in the mounting place.

In the constitution of the foregoing modification example, the flow path members Rm disposed on the identification portions 231 to 235 may be indicated in the same color as the identification portions where they are disposed (may be colored in different colors). That is, the flow path members disposed on the respective identification portions may be indicated in different colors (may be colored in different colors).

The flow path member R1 disposed on the identification portion 231 may be indicated in red, for example.

The flow path member R2 disposed on the identification portion 232 may be indicated in blue, for example.

The flow path member R1 disposed on the identification portion 233 may be indicated in red, for example.

The flow path member R2 disposed on the identification portion 234 may be indicated in blue, for example.

The flow path member R5 disposed on the identification portion 235 may be indicated in yellow, for example.

The worker does not necessarily need to dispose all the flow path members Rm exactly on the identification portions 231 to 234, and part of the flow path members Rm may be disposed in the vicinity of the identification portions 231 to 234.

Some or all of the identification portions 231 to 235 may not be classified by color.

The identification portions 231 to 235 are indicated by lines having different shapes. However, some or all of them may be indicated by lines having the same shape (for example, solid lines), or some or all of them may not be provided.

Some or all of the identification portions 231 to 235 may include no character portion.

Some or all of the arrow portions 236 to 239 may not be classified by color, or some or all of them may not be provided.

Since the flow path member R5 for circulating air is disposed on the identification portion 235, the identification portion 235 includes no arrow portion, but it may include an arrow portion. In this case, the arrow portion of the identification portion 235 indicates a direction in which air circulates through the flow path member R5.

Modification Example 4

A modification example of the instrument attachment section 21 according to the present invention is described below.

Figure 21:
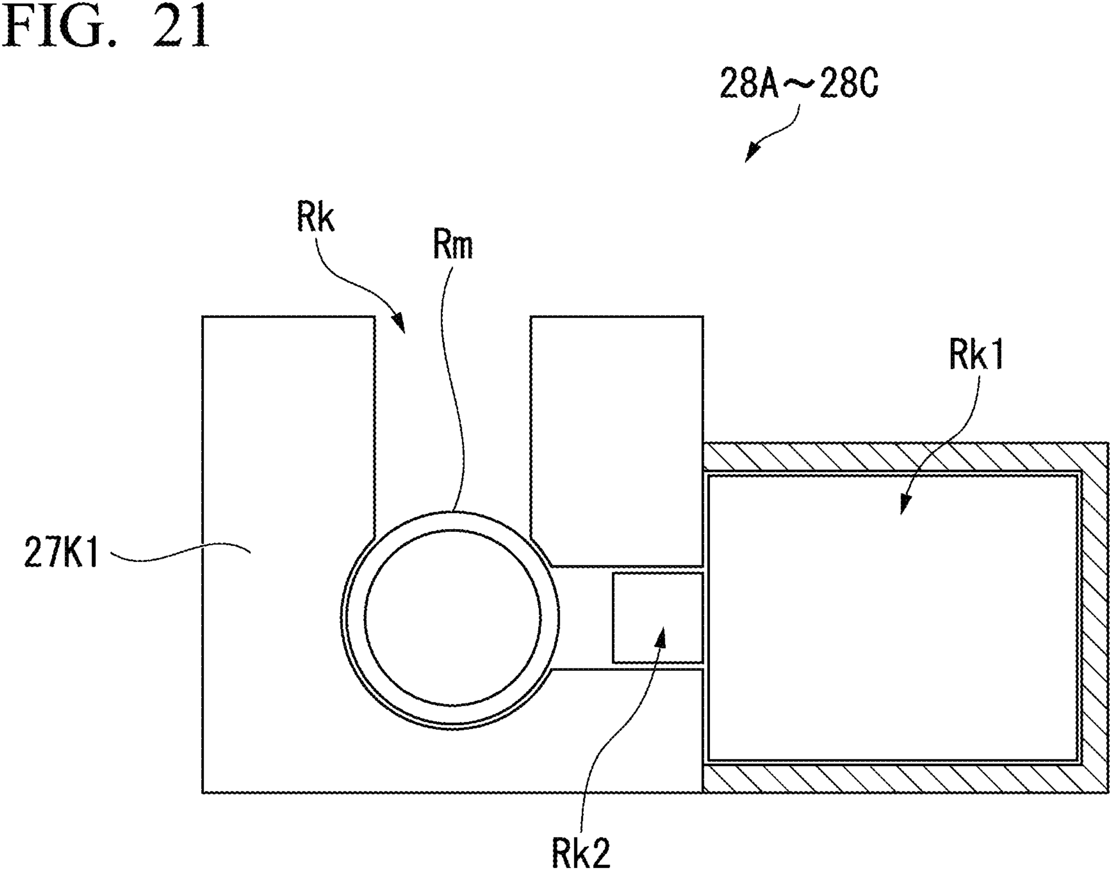
FIG. 21 is a view showing the instrument attachment section according to Modification Example 4 of the present invention.

As shown in FIG. 21, the liquid detection portions 28 (the concentration meter 28A, the pressure sensor 28B, and the liquid detection sensor 28C) according to the present modification example each include a clamp portion 27K1 which clamps the flow path member Rm, an amplifier Rk1, and a light projection/reception portion Rk2.

The liquid detection portions 28 are provided between other control instruments.

The flow path member Rm is mounted in the clamp portion 27K1 as a flow path holding portion Rk.

The clamp portion 27K1 opens outward on the side surface of the casing 20, and the flow path member Rm passes through the opening of the clamp portion 27K1 and is constituted in an attachable/detachable manner at the clamping position of the clamp portion 27K1.

The amplifier Rk1 and the light projection/reception portion Rk2 integrally function as a light projector which projects light onto a liquid circulating through the flow path members Rm and a light receiver which receives reflected light from a liquid circulating through the flow path members Rm.

Due to such a constitution, in the present modification example, the liquid detection portions 28 provided between other control instruments include the amplifier Rk1 and the light projection/reception portion Rk2 which integrally function as a light projector and a light receiver. Therefore, the liquid detection portions 28 can detect a liquid circulating through the flow path members Rm more exactly.

Hereinabove, an embodiment of the present invention and modification examples thereof are described. However, the present invention is not limited to the foregoing embodiment and the modification examples thereof, can be suitably changed within a range not departing from the gist thereof, and includes a combination thereof.

For example, the ultrasonic device 1 may have a constitution in which the fluid circuit section 25 provided on the casing 20 (casing main body 20A) includes the instrument attachment section 210 according to the foregoing Modification Example 2 and the upper surface of the casing 20 (casing main body 20A) is the upper surface 230 according to the foregoing Modification Example 3.

INDUSTRIAL APPLICABILITY

The present invention can be utilized in an ultrasonic therapy device, a fluid operation device, and a fluid circuit set in which work efficiency of replacement work and work of supplying and discharging a medium liquid when a contact member, flow path members of a fluid circuit section, and a liquid container for circulating a liquid are replaced for each therapy can be improved.

REFERENCE SIGNS LIST

1 Ultrasonic therapy device
2 Robot arm
3-*n* Arm member
10 Ultrasonic head unit
11A Wave source
12 Liquid storage section
14 Contact member
14A Contact portion
14B Mounting portion
14P Connection member
14Q Tubular portion
14R Connection portion
14RA Inflow connection portion
14RB Outflow connection portion
20 Casing
21 Instrument attachment section
21A First attachment portion
21B Second attachment portion
21K Detachable engagement portion
21P Detachable attachment member
21R1 to 21R9 First cutout portion to ninth cutout portion
21Ro Plurality of cutout portions
21S Circuit control instrument section
22 Rotation support portion
23 Support portion
25 Fluid circuit section
25A First circuit portion
25A1 Inflow circuit portion
25A2 Outflow circuit portion
25A3 Discharge circuit portion
25B Second circuit portion
29 Liquid container
29B Engagement portion
29C Connection portion
29D First connection portion
29E Second connection portion
42 Control section
Rm Flow path member

The invention claimed is:

1. An ultrasonic therapy device comprising:

a robot arm that includes a plurality of arms joined with a plurality of joints, moves a holding target to an arbitrary position, and is configured for holding the holding target in an arbitrary posture state;

an ultrasonic head that is held by the robot arm and includes a wave source which radiates ultrasonic waves in a manner of focusing at a predetermined position inside a therapy object and a liquid storage section which includes a contact portion whose lower surface side comes into contact with the therapy object and is formed to have an adjustable volume; and a fluid circuit that includes a plurality of flow path members for circulating a medium liquid which fills the liquid storage section and transmits the ultrasonic waves, wherein the fluid circuit includes a circuit control instrument which causes the medium liquid to circulate through the plurality of flow path members, and an instrument attachment section on which the circuit control instrument is attached at a predetermined position, the circuit control instrument is attached to one surface side of the instrument attachment section, and the plurality of flow path members are provided in an attachable/detachable manner with respect to the circuit control instrument, the fluid circuit includes a first circuit which causes the medium liquid to circulate through the plurality of flow path members, and a second circuit which causes gas to flow into the first circuit from an outside, and the first circuit includes an inflow circuit which causes the medium liquid to flow into the liquid storage section, an outflow circuit which causes the medium liquid to flow out from the liquid storage section, and a discharge circuit which discharges the medium liquid to the outside, and the ultrasonic therapy device further comprises:

a casing that is provided with the instrument attachment section such that the one surface side of the instrument attachment section faces the outside; and a rotation support that is provided on the casing and rotatably supports the instrument attachment section.

2. The ultrasonic therapy device according to claim 1 further comprising:

a support that is provided on the casing and engages with and supports a liquid container which accommodates the medium liquid, wherein a medium liquid unit including the medium liquid supplied to the fluid circuit engages with the support, the medium liquid unit includes the liquid container which accommodates the medium liquid, and a connector which connects the liquid container and the fluid circuit, the liquid container is provided with an engagement portion which engages with the support, the connector includes a first connector which is connected to the inflow circuit, and a second connector which is connected to the outflow circuit, and the medium liquid is degassed water from which dissolved gas is removed.

3. The ultrasonic therapy device according to claim 1, wherein the casing further includes a plurality of flow path supports on an upper surface thereof, and the plurality of flow path supports disposed on the upper surface of the casing surround a projection region on the upper surface of the casing which coincides with a predetermined position in the ultrasonic head in a view in an up-down direction.

4. An ultrasonic therapy device comprising:

a robot arm that includes a plurality of arm joined with a plurality of joints, moves a holding target to an arbitrary position, and is configured for holding the holding target in an arbitrary posture state;

an ultrasonic head that is held by the robot arm and includes a wave source which radiates ultrasonic waves in a manner of focusing at a predetermined position inside a therapy object and a liquid storage section which includes a contact portion whose lower surface side comes into contact with the therapy object and is formed to have an adjustable volume; and a fluid circuit that includes a plurality of flow path members for circulating a medium liquid which fills the liquid storage section and transmits the ultrasonic waves, wherein the fluid circuit includes a circuit control instrument which causes the medium liquid to circulate through the plurality of flow path members, and an instrument attachment section on which the circuit control instrument is attached at a predetermined position, the circuit control instrument is attached to one surface side of the instrument attachment section, and the plurality of flow path members are provided in an attachable/detachable manner with respect to the circuit control instrument, the fluid circuit includes

- a first circuit which causes the medium liquid to circulate through the plurality of flow path members, and
- a second circuit which causes gas to flow into the first circuit from an outside, and the first circuit includes

- an inflow circuit which causes the medium liquid to flow into the liquid storage section,
- an outflow circuit which causes the medium liquid to flow out from the liquid storage section, and
- a discharge circuit which discharges the medium liquid to the outside the instrument attachment section includes

- a first attachment portion to which the circuit control instrument is attached, and
- a second attachment portion which is provided in an attachable/detachable manner with respect to the first attachment portion, the first attachment portion includes a detachable engagement portion which causes the second attachment portion to be engaged and positionally set at a predetermined position, the second attachment portion includes a detachable attachment member to which the plurality of flow path members are attached, and on the detachable attachment member, a mounting engagement portion which engages with the detachable engagement portion is formed.

5. The ultrasonic therapy device according to claim 4, wherein in the detachable attachment member, the plurality of flow path members are positionally set and attached in a state of being exposed at a plurality of predetermined positions, and at the plurality of predetermined positions, cutouts are formed as necessary at positions corresponding to positions of control instruments included in the circuit control instrument.

6. The ultrasonic therapy device according to claim 4, wherein on the detachable attachment member, a plurality of flow path supports which positionally set the plurality of flow path members at a plurality of predetermined positions are provided, at the plurality of predetermined positions, cutouts are formed as necessary at positions corresponding to positions of control instruments included in the circuit control instrument, and the plurality of flow path members are disposed so as to be exposed through the cutouts.

7. The ultrasonic therapy device according to claim 6, wherein at least some of the plurality of flow path supports are disposed at positions on an upstream side and a downstream side of the positions of the control instruments in a circulation direction in which the medium liquid circulates through the plurality of flow path members.

8. The ultrasonic therapy device according to claim 4, wherein at least one of the first attachment portion and the second attachment portion includes

- an inflow identification portion which guides the inflow circuit,
- an outflow identification portion which guides the outflow circuit, and
- a discharge identification portion which guides the discharge circuit.

9. The ultrasonic therapy device according to claim 8, wherein the inflow identification portion, the outflow identification portion, and the discharge identification portion are indicated in different colors, in the plurality of flow path members, the flow path member forming the inflow circuit, the flow path member forming the outflow circuit, and the flow path member forming the discharge circuit are indicated in different colors, the inflow identification portion and the flow path member forming the inflow circuit are indicated in the same color, the outflow identification portion and the flow path member forming the outflow circuit are indicated in the same color, and the discharge identification portion and the flow path member forming the discharge circuit are indicated in the same color.

10. The ultrasonic therapy device according to claim 8, wherein the inflow identification portion, the outflow identification portion, and the discharge identification portion respectively have arrows which indicate a circulation direction of the medium liquid circulating through the flow path members which are respectively disposed thereon.

11. The ultrasonic therapy device according to claim 8, wherein the inflow identification portion, the outflow identification portion, and the discharge identification portion respectively have character portions which indicate targets to which the flow path members, which are respectively disposed thereon, are connected or substances which circulate through the flow path members which are respectively disposed thereon.

12. The ultrasonic therapy device according to claim 8, wherein at least the one of the first attachment portion and the second attachment portion further includes a second-circuit-portion identification portion which guides the second circuit, and the second-circuit-portion identification portion is indicated by a line having a shape different from those of the inflow identification portion, the outflow identification portion, and the discharge identification portion.

13. An ultrasonic therapy device comprising:

a robot arm that includes a plurality of arm joined with a plurality of joints, moves a holding target to an arbitrary position, and is configured for holding the holding target in an arbitrary posture state;

an ultrasonic head that is held by the robot arm and includes a wave source which radiates ultrasonic waves in a manner of focusing at a predetermined position inside a therapy object and a liquid storage section which includes a contact portion whose lower surface side comes into contact with the therapy object and is formed to have an adjustable volume;

a fluid circuit that includes a plurality of flow path members for circulating a medium liquid which fills the liquid storage section and transmits the ultrasonic waves; and a control section that controls the fluid circuit to adjust a storage amount of the medium liquid stored in the liquid storage section, and to discharge the medium liquid from the fluid circuit and supply a new medium liquid to the fluid circuit, wherein the fluid circuit includes a circuit control instrument which causes the medium liquid to circulate through the plurality of flow path members, and an instrument attachment section on which the circuit control instrument is attached at a predetermined position, the circuit control instrument is attached to one surface side of the instrument attachment section, and the plurality of flow path members are provided in an attachable/detachable manner with respect to the circuit control instrument, the fluid circuit includes a first circuit which causes the medium liquid to circulate through the plurality of flow path members, and a second circuit which causes gas to flow into the first circuit from an outside, and the first circuit includes an inflow circuit which causes the medium liquid to flow into the liquid storage section, an outflow circuit which causes the medium liquid to flow out from the liquid storage section, and a discharge circuit which discharges the medium liquid to the outside, the ultrasonic therapy device further comprises:

a contact member that is attached to the liquid storage section and included in the liquid storage section accommodating the medium liquid;

a liquid container that is connected to the fluid circuit and accommodates the medium liquid supplied to the fluid circuit, the contact member includes the contact portion which is provided in a lower portion of the contact member, and a mounting portion which is formed to extend in a manner of surrounding an upper part around the contact portion and mounted on a mounting target part of the ultrasonic head, and the mounting portion includes an inflow connector which is provided at a first position and connected to the inflow circuit, and an outflow connector which is provided at a second position different from the first position in a plan view and connected to the outflow circuit, and the control section controls the robot arm such that the ultrasonic head is held in a first posture, in which the contact portion faces downward and the outflow connector is located on a side higher than the inflow connector, and controls the fluid circuit such that the medium liquid is supplied to the liquid storage section in a liquid supplying step at a time of preparation for therapy, and controls the robot arm such that the ultrasonic head is held in a second posture, in which the contact portion faces upward and the outflow connector is located on a side lower than the inflow connector, and controls the fluid circuit such that the medium liquid is discharged from the liquid storage section in a liquid discharging step at the time of the preparation for therapy.

14. The ultrasonic therapy device according to claim 13, wherein the inflow connector and the outflow connector each include a tubular portion of which one end side is connected to the mounting portion, and a connector which is provided on the other end side of the tubular portion and connected to the fluid circuit, and the inflow connector and the outflow connector are adjacently provided along the mounting portion.

15. A fluid operation device used in an ultrasonic head that includes a wave source which radiates ultrasonic waves in a manner of focusing at a predetermined position inside a therapy object and a liquid storage section which includes a contact portion whose lower surface side comes into contact with the therapy object and is formed to have an adjustable volume, the fluid operation device comprising:

a fluid circuit that includes a plurality of flow path members for circulating a medium liquid which fills the liquid storage section and transmits the ultrasonic waves, wherein the fluid circuit includes a circuit control instrument which causes the medium liquid to circulate through the plurality of flow path members, and an instrument attachment section on which the circuit control instrument is attached at a predetermined position, the circuit control instrument is attached to one surface side of the instrument attachment section, and the plurality of flow path members are provided in an attachable/detachable manner with respect to the circuit control instrument, the fluid circuit includes a first circuit which causes the medium liquid to circulate through the plurality of flow path members, and a second circuit which causes gas to flow into the first circuit from an outside, the first circuit includes an inflow circuit which causes the medium liquid to flow into the liquid storage section, an outflow circuit which causes the medium liquid to flow out from the liquid storage section, and a discharge circuit which discharges the medium liquid to the outside, the instrument attachment section includes a first attachment portion to which the circuit control instrument is attached, and a second attachment portion which is provided on an attachable/detachable manner with respect to the first attachment portion, the first attachment portion includes a detachable engagement portion which causes the second attachment portion to be engaged and positionally set at a predetermined position, the second attachment portion includes a detachable attachment member to which the plurality of flow path members are attached, on the detachable attachment member, a mounting engagement portion which engages with the detachable engagement portion is formed, and a plurality of flow path supports which positionally set the plurality of flow path members at a plurality of predetermined positions are provided, at the plurality of predetermined positions, cutouts are formed as necessary at positions corresponding to positions of control instruments in the circuit control instrument, and the plurality of flow path members are disposed so as to be exposed through the cutouts.

16. An ultrasonic therapy device comprising:

a robot arm that includes a plurality of arm joined with a plurality of joints, moves a holding target to an arbitrary position, and is configured for holding the holding target in an arbitrary posture state;

an ultrasonic head that is held by the robot arm and includes a wave source which radiates ultrasonic waves in a manner of focusing at a predetermined position inside a therapy object and a liquid storage section which includes a contact portion whose lower surface side comes into contact with the therapy object and is formed to have an adjustable volume; and a fluid circuit that includes a plurality of flow path members for circulating a medium liquid which fills the liquid storage section and transmits the ultrasonic waves, wherein the fluid circuit includes a circuit control instrument which causes the medium liquid to circulate through the plurality of flow path members, and an instrument attachment section on which the circuit control instrument is attached at a predetermined position, the circuit control instrument is attached to one surface side of the instrument attachment section, and the plurality of flow path members are provided in an attachable/detachable manner with respect to the circuit control instrument, the fluid circuit includes a first circuit which causes the medium liquid to circulate through the plurality of flow path members, and a second circuit which causes gas to flow into the first circuit from an outside, the first circuit includes an inflow circuit which causes the medium liquid to flow into the liquid storage section, an outflow circuit which causes the medium liquid to flow out from the liquid storage section, and a discharge circuit which discharges the medium liquid to the outside, the inflow circuit includes a first flow path member, of the plurality of flow path members, which causes the medium liquid to flow into the liquid storage section, the outflow circuit includes a second flow path member, of the plurality of flow path members, which causes the medium liquid to flow out from the liquid storage section, and a third flow path member, of the plurality of flow path members, which bypasses a part in the middle of the second flow path member, a liquid supply pump which supplies the medium liquid to the liquid storage section in the inflow circuit is provided in the middle of the first flow path member, and a liquid discharge pump which discharges the medium liquid from the liquid storage section in the outflow circuit is provided in the middle of the third flow path member.

17. A fluid operation device used in an ultrasonic head that includes a wave source which radiates ultrasonic waves in a manner of focusing at a predetermined position inside a therapy object and a liquid storage section which includes a contact portion whose lower surface side comes into contact with the therapy object and is formed to have an adjustable volume, the fluid operation device comprising:

a fluid circuit that includes a plurality of flow path members for circulating a medium liquid which fills the liquid storage section and transmits the ultrasonic waves, wherein the fluid circuit includes a circuit control instrument which causes the medium liquid to circulate through the plurality of flow path members, and an instrument attachment section on which the circuit control instrument is attached at a predetermined position, the circuit control instrument is attached to one surface side of the instrument attachment section, and the plurality of flow path members are provided in an attachable/detachable manner with respect to the circuit control instrument, the fluid circuit includes a first circuit which causes the medium liquid to circulate through the plurality of flow path members, and a second circuit which causes gas to flow into the first circuit from an outside, the first circuit includes an inflow circuit which causes the medium liquid to flow into the liquid storage section, an outflow circuit which causes the medium liquid to flow out from the liquid storage section, and a discharge circuit which discharges the medium liquid to the outside, the fluid operation device further comprises:

a control section that controls the circuit control instrument, the circuit control instrument includes a plurality of pinch valves which stop circulation of the medium liquid in the flow path members or release the stop, the control section is configured to release the stop of all the pinch valves so as configured to replace the instrument attachment section, and the control section controls the circuit control instrument to adjust a storage amount of a medium liquid stored in the liquid storage section, discharge the medium liquid from the fluid circuit, and supply a new medium liquid to the fluid circuit.

18. The fluid operation device according to claim 17, wherein the circuit control instrument further includes a plurality of pumps which cause the medium liquid in the flow path members to circulate, and a plurality of liquid detectors which detect the medium liquid circulating through the flow path members, the liquid detectors are respectively provided in at least the plurality of pumps and the plurality of pinch valves, and the control section controls a flow of the medium liquid circulating through the flow path members of the fluid circuit by controlling the circuit control instrument which includes the plurality of liquid detectors, the plurality of pumps and the plurality of pinch valves.

* * * * *